United States Patent [19]

Takagi et al.

[11] Patent Number: 5,543,573
[45] Date of Patent: Aug. 6, 1996

[54] HYDRAZINECARBOXYAMIDE DERIVATIVES, A PROCESS FOR PRODUCTION THEREOF AND USES THEREOF

[75] Inventors: Kazuhiro Takagi; Takashi Ohtani, both of Nishinomiya; Tateki Nishida, Yawata; Hiroshi Hamaguchi, Kyoto; Tetsuyoshi Nishimatsu; Atsushi Kanaoka, both of Kawachinagano, all of Japan

[73] Assignee: Nihon Nohyaku Co., Ltd., Tokyo, Japan

[21] Appl. No.: 227,701

[22] Filed: Apr. 14, 1994

Related U.S. Application Data

[63] Continuation of Ser. No. 13,197, Jan. 29, 1993, abandoned, which is a continuation of Ser. No. 711,138, Jun. 6, 1991, abandoned.

[30]  Foreign Application Priority Data

Jun. 16, 1990 [JP] Japan ..................................... 2-158414
Jun. 23, 1990 [JP] Japan ..................................... 2-164964

[51] Int. Cl.⁶ ..................................................... A01N 9/12
[52] U.S. Cl. .............................. 514/590; 564/18; 564/20; 564/34; 564/290; 558/406; 558/408; 558/417
[58] Field of Search .............................. 564/290, 36, 34, 564/18, 20; 558/417

[56]  References Cited

U.S. PATENT DOCUMENTS

3,885,042  5/1975  Mudler et al. ........................... 424/323
4,983,755  1/1991  Bühmann et al. ....................... 424/323

FOREIGN PATENT DOCUMENTS

0144853  5/1985  European Pat. Off. ..
WO92/06076  4/1992  European Pat. Off. ..
2304789  8/1973  Germany .
48-14359  2/1973  Japan .
54-119029  9/1979  Japan .
63-93761  4/1988  Japan .
1314899  4/1973  United Kingdom .

OTHER PUBLICATIONS

Chemical Abstract, vol. 85, 1976, Tomchin et al., Zh. Org. Khim, 12(4), 851–5, p. 632.
Patent Abstract of Japan No. 54119019, vol. 3, No. 138 (September 1979).
Chemical Abstract No. 184780, vol. 110, No. 20 (May 1989).
Chemical Abstract of Japan, Abstract No. 94317p, vol. 85, No. 13 (September 1976).
Chemical Abstracts, CA95 (13): 94317P, Tomchin et al., "Semicarbazones... of the acyclic and carboxylic series", Zh. Org. Khim, 17(4), 851–5, Russ, 1976.
AN 100: 184892 Chemical Abstracts. El–Asmy et al, "Physical, Chemical, and Biological Studies on Transition Metal Complexes of Chelatiz Fridentats Lijanl" *Transition metal chem.* (London) (1988), 13(5), pp. 332–5. Abstract only.

*Primary Examiner*—Marianne M. Cintins
*Assistant Examiner*—Keith MacMillan
*Attorney, Agent, or Firm*—Cushman Darby & Cushman

[57]  ABSTRACT

The present invention relates to a hydrazinecarboxamide derivative of the general formula (I) shown below:

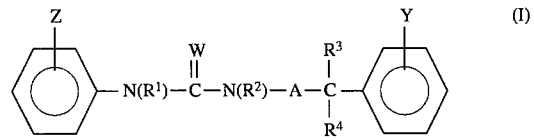

wherein the substituents are as defined in the specification, which has a wide insecticidal spectrum at a low dosage, a process for producing said derivative, and utilization of said derivative as an insecticide.

7 Claims, No Drawings

HYDRAZINECARBOXYAMIDE DERIVATIVES, A PROCESS FOR PRODUCTION THEREOF AND USES THEREOF

This is a continuation of application Ser. No. 08/013,197, filed on Jan. 29, 1993, which is abandoned, which is a continuation of application No. 07/711,138, filed Jun. 6, 1991, abandoned.

BACKGROUND OF THE INVENTION

1. Field of the Invention

This invention relates to hydrazinecarboxamide derivatives, in particular, compounds having a wide insecticidal spectrum.

2. Related Art

Jap. Pat. Appln. Kokai (Laid-Open) No. 48-91223 discloses that semicarbazides are effective as insecticides. Jap. Pat. Appln. Kokai (Laid-Open) No. 54-119029 discloses that thiosemicarbazones are useful as agricultural and horticultural disease-controlling agents. Jap. Pat. Appln. Kokai (Laid-open) No. 63-93761 discloses that substituted hydrazones are effective as pest-controlling agents.

However, a compound having a wide insecticidal spectrum has not yet been disclosed.

SUMMARY OF THE INVENTION

The present inventors earnestly investigated in order to develop a novel insecticide and consequently found that a hydrazinecarboxamide derivative represented by the general formula (I) shown below has an excellent insecticidal effect at a low dosage, whereby the present invention was accomplished.

That is, the present invention relates to a hydrazinecarboxamide derivative represented by the general formula (I):

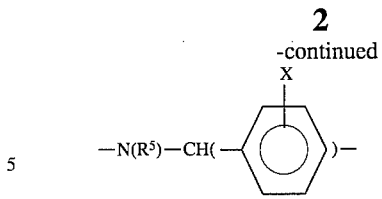

wherein $R^1$ is a hydrogen atom or a lower alkyl group, $R^2$ is a hydrogen atom or a lower alkyl group, $R^3$ is a hydrogen atom; a hydroxyl group; a lower alkyl group; a lower alkoxy group; a lower alkylcarbonyloxy group; an unsubstituted phenylcarbonyloxy group; or a substituted phenylcarbonyloxy group having on the phenyl ring 1 to 5 substituents which may be the same or different and are selected from the group consisting of halogen atoms, lower alkyl groups and lower haloalkyl groups, $R^4$ is a hydrogen atom or a lower alkyl group, $R^3$ and $R^4$ being able to be taken together to represent an oxygen atom, A is

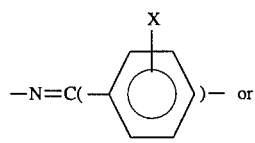 or

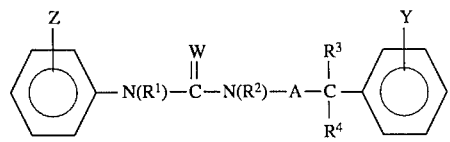

(wherein X represents 1 to 5 atoms or groups which may be the same or different and are selected from the group consisting of hydrogen atom; hydroxyl group; halogen atoms; cyano group; lower alkyl groups; lower haloalkyl groups; lower alkoxy groups; lower haloalkoxy groups; lower alkoxyalkyl groups; lower alkenyloxy groups; cycloalkylcarbonyloxy groups; lower alkoxycarbonyloxy groups; lower alkoxycarbonylalkyloxy groups; lower alkylcarbonylalkyloxy groups; lower alkylsulfonyloxy groups; phenoxy group; methylenedioxy group; alkenylene groups having 3 to 4 carbon atoms so as to form a polycyclic ring together with the adjacent carbon atom of the phenyl ring; unsubstituted amino group; substituted amino groups having as the substituent(s) 1 or 2 lower alkyl groups which may be the same or different; substituted aminocarbonyloxy groups having as the substituent(s) 1 or 2 lower alkyl groups which may be the same or different; and dioxolane group, and $R^5$ is a hydrogen atom; a lower alkylcarbonyl group; a lower haloalkylcarbonyl group; a cycloalkylcarbonyl group; a lower alkoxycarbonyl group; a lower alkoxydicarbonyl group; an unsubstituted phenylcarbonyl group; substituted phenylcarbonyl groups having 1 to 5 substituents which may be the same or different and are selected from the group consisting of halogen atoms, lower alkyl groups, lower haloalkyl groups, lower alkoxy groups and lower haloalkoxy groups; or a substituted aminocarbonyl group having 1 or 2 substituents which may be the same or different and are selected from the group consisting of hydrogen atom, lower alkyl groups, unsubstituted phenyl group, and substituted phenyl groups having 1 to 5 substituents which may be the same or different and are selected from halogen atoms, lower alkyl groups, lower haloalkyl groups, lower alkoxy groups and lower haloalkoxy groups), Y represents 1 to 5 atoms or groups which may be the same or different and are selected from the group consisting of hydrogen atom; hydroxyl group; halogen atoms; cyano group; nitro group; alkyl groups; lower haloalkyl groups; lower alkoxy groups; lower haloakoxy groups; lower alkenyloxy groups; lower alkylcarbonyloxy groups; lower alkylsulfonyloxy groups; lower haloalkylsulfonyloxy groups; lower alkylthio groups; lower haloalkylthio groups; lower alkylsulfinyl groups; lower haloalkylsulfinyl groups; lower alkylsulfonyl groups; lower haloalkylsulfonyl groups; lower alkoxycarbonyl groups; unsubstituted amino group; substituted amino groups having 1 or 2 substituents selected from the group consisting of formyl group, lower alkylcarbonyl groups, lower alkylsulfonyl groups, and substituted aminocarbonyl groups having as the substituent(s) one or more lower alkyl groups which may be the same or different; unsubstituted aminocarbonyl group; substituted aminocarbonyl groups having as the substituent(s) 1 or 2 lower alkyl groups which may be the same or different; substituted aminosulfonyl groups having as the substituent(s) 1 or 2 lower alkyl groups which may be the same or different; phenyl group; or azaalkenylene groups having 2 to 3 carbon atoms so as to form a polycyclic ring together with the adjacent carbon atom of the phenyl ring, Z represents 1 to 5 atoms or groups which may be the same or different and are selected from the group consisting of hydrogen atom; halogen atoms; cyano group; nitro group; alkyl groups; lower haloalkyl groups; unsubstituted cycloalkyl groups; substituted cycloalkyl groups having 1 to 5 substituents which may be the same or different and are selected from the group consisting of halogen atoms and lower alkyl groups; lower alkoxy groups; lower haloalkoxy groups; lower alkylthio groups; lower haloalkylthio groups; lower alkylsulfinyl groups; lower haloalkylsulfinyl groups; lower alkylsulfonyl groups; lower haloalkylsulfonyl groups; lower alkylcarbonyl groups; lower alkoxycarbonyl groups; lower alkylcarbonyloxy groups; lower alkylsulfonyloxy groups; lower haloalkylsulfonyloxy groups; unsubstituted phenoxy group; substituted phenoxy groups having 1 to 5 substituents which may be the same or different and are selected from the group consisting of halogen atoms, lower alkyl groups, lower haloalkyl groups, lower alkoxy groups and lower haloalkoxy groups; unsubstituted pyridyloxy group; substituted pyridyloxy groups having as the substituent(s) 1 to 4 atoms or groups which may be the same or different and are selected from the group consisting of halogen atoms, lower alkyl groups, lower haloalkyl groups, lower alkoxy groups and lower haloalkoxy groups, and W is an oxygen atom or a sulfur atom. The present invention further relates to a process for producing said derivative, and an agricultural and horticultural insecticide containing said derivative as an active ingredient.

In the definition of the substituents of the hydrazinecarboxamide derivative of the general formula (I), the term "lower" is used for expressing a number of carbon atoms of 1 to 6, and the prefix "halo" is used for expressing that a group has as its substituent(s) one or more halogen atoms which may be the same or different and are selected from the group consisting of chlorine atom, fluorine atom, bromine atom and iodine atom.

Of the hydrazinecarboxamide derivatives of the general formula (I) of the present invention, a hydrazinecarboxamide derivative of the genera formula (1') shown hereinafter has geometrical isomers, i.e., E-form and Z-form. The present invention also includes the E-form, the Z-form and mixtures comprising the E-form and Z-form in an arbitrary ratio. Each of hydrazinecarboxamide derivatives of the general formulas (I") and (I''') shown hereinafter have stereoisomers, i.e., R-form and S-form. The present invention also includes the R-form, the S-form and mixtures comprising the R-form and the S-form in an arbitrary ratio.

All of the hydrazinecarboxamide derivatives of the general formulas (I'), (I") and (I''') are included in the hydrazinecarboxamide derivatives of the general formula (I).

DETAILED DESCRIPTION OF PREFERRED EMBODIMENTS

Preferable examples of the substituents of the hydrazinecarboxamide derivative of the above general formula (I) of the present invention are as follows. $R^1$, $R^2$, $R^3$ and $R^4$, which may be the same or different are preferably hydrogen atoms; hydroxyl groups; or lower alkyl groups such as methyl, ethyl, n-propyl, i-propyl, n-butyl, i-butyl, s-butyl, t-butyl, etc. Preferable examples of substituent(s) for X are a hydrogen atom; halogen atoms such as chlorine, fluorine, bromine, iodine, etc.; a cyano group; lower alkyl groups such as methyl, ethyl, n-propyl, i-propyl, n-butyl, i-butyl, s-butyl, t-butyl, etc.; lower haloalkyl groups such as dichloromethyl, difluoromethyl, trichloromethyl, trifluoromethyl, difluoroethyl, trifluoroethyl, tetrafluoroethyl, etc.; lower alkoxy groups such as methoxy, ethoxy, propoxy, etc.; and lower haloalkoxy groups such as difluoromethoxy, trifluoromethoxy, difluoroethoxy, trifluoroethoxy, etc. As to the position(s) of the substituent(s) for X, at least one substituent is preferably at the 3-position.

Preferable examples of substituent(s) for Y are a hydrogen atom; halogen atoms such as chlorine, fluorine, bromine, iodine, etc.; a cyano group; a nitro group; alkyl groups such as methyl, ethyl, n-propyl, i-propyl, n-butyl, i-butyl, s-butyl, t-butyl, pentyl, heptyl, etc.; lower haloalkyl groups such as dichloromethyl, difluoromethyl, trichloromethyl, trifluoromethyl, difluoroethyl, trifluoroethyl, tetrafluoroethyl, etc.; lower alkoxy groups such as methoxy, ethoxy, propoxy, etc.; lower haloalkoxy groups such as difluoromethoxy, trifluoromethoxy, difluoroethoxy, trifluoroethoxy, etc.; lower alkylsulfonyloxy groups such as methyl sulfonyloxy, etc.; lower haloalkylsulfonyloxy groups such as trifluoromethyl sulfonyloxy, etc.; and lower alkoxycarbonyl groups such as methoxycarbonyl, etc. As to the position(s) of the substituent(s) for Y, at least one substituent is preferably at the 4-position. A particularly preferable example of the substituent(s) for Y is a cyano group.

Preferable examples of substituent(s) for Z are a hydrogen atom; halogen atoms such as chlorine, fluorine, bromine, iodine, etc.; a cyano group; alkyl groups such as methyl, ethyl, n-propyl, i-propyl, n-butyl, i-butyl, s-butyl, t-butyl, pentyl, heptyl, etc.; lower haloalkyl groups such as dichloromethyl, difluoromethyl, trichloromethyl, trifluoromethyl, difluoroethyl, trifluoroethyl, tetrafluoroethyl, etc.; lower alkoxy groups such as methoxy, ethoxy, propoxy, butoxy, etc.; lower haloalkoxy groups such as dichloromethoxy, difluoromethoxy, trichloromethoxy, trifluoromethoxy, difluoroethoxy, trifluoroethoxy, tetrafluoroethoxy, etc.; lower alkylthio groups such as methylthio, ethylthio, etc.; lower haloalkylthio groups such as difluoromethylthio, trifluoromethylthio, trifluoroethylthio, tetrafluoroethylthio, etc., lower alkylsulfinyl groups such as methylsulfinyl, ethylsulfinyl, etc.; lower haloalkylsulfinyl groups such as difluoromethylsulfinyl, trifluoromethylsulfinyl, trifluoroethylsulfinyl, tetrafluoroethylsulfinyl, etc.; lower alkylsulfonyl groups such as methylsulfonyl, ethylsulfonyl, etc.; and lower haloalkylsulfonyl groups such as difluoromethylsulfonyl, trifluoromethylsulfonyl, trifluoroethylsulfonyl, tetrafluoroethylsulfonyl, etc. As to the position(s) of the substituent(s) for Z, at least one substituent is preferably at the 4-position.

$R^5$ is preferably a hydrogen atom; a lower alkylcarbonyl group such as methylcarbonyl, ethylcarbonyl or the like; a lower haloalkylcarbonyl group such as difluoromethylcarbonyl, trifluoromethylcarbonyl, tetrafluoroethylcarbonyl, or the like; or a lower alkoxycarbonyl group such as methoxycarbonyl, ethoxycarbonyl, propoxycarbonyl, or the like. W is preferably an oxygen atom. However, the substituents of the hydrazinecarboxamide derivative of the general formula (I) of the present invention are not limited to the above-exemplified atoms and groups.

As to typical processes for producing the hydrazinecarboxamide derivative of the general formula (I) of the present invention, said derivative can be produced, for example, by the production processes illustrated below.

Process A

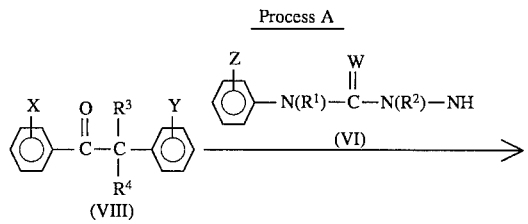

-continued
Process A

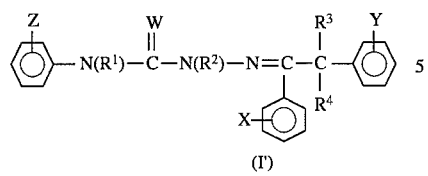
(I')

wherein $R^1$, $R^2$, $R^3$, $R^4$, X, Y, Z and W have the same meanings as those defined above.

A hydrazinecarboxamide derivative of the general formula (I') can be produced by reacting a compound of the general formula (VIII) with a compound of the general formula (VI) in the presence of an inert solvent and in the presence or absence of a catalyst.

Reaction A-1.

General formula (VIII)→general formula (I')

As the inert solvent used in this reaction, any inert solvent may be used so long as it does not markedly inhibit the progress of the reaction. There can be exemplified alcohols such as methanol, ethanol, propanol, butanol, etc.; halogenated hydrocarbons such as dichloromethane, chloroform, carbon tetrachloride, etc.; aromatic hydrocarbons such as benzene, toluene, xylene, etc.; nitriles such as acetonitrile, benzonitrile, etc.; ethers such as Methyl Cellosolve, diethyl ether, diglyme, dioxane, tetrahydrofuran, etc.; carboxylic acids such as acetic acid, etc.; dimethylacetamide; dimethyl sulfoxide; and water.

These inert solvents may be used singly or as a mixture thereof.

As the catalyst used in the reaction, there can be used, for example, inorganic acids such as hydrochloric acids, sulfuric acid and the like, or organic acids such as p-toluenesulfonic acid and the like.

As to the amount of the catalyst used, it is sufficient that the catalyst is present in the reaction system in an amount of 0.001 to 10% by weight based on the weight of the compound of the general formula (VIII).

Although the reactants are used in equimolar amount because the reaction is an equimolar reaction, either of them may be used in excess.

The reaction temperature may be properly chosen in the range of room temperature to the boiling range of the inert solvent used. The reaction is carried out preferably at 70° to 80° C.

Although the reaction time is varied depending on the degree of reaction, the reaction temperature, and the like, it may be chosen in the range of several minutes to 48 hours.

After completion of the reaction, the desired compound is isolated from a reaction solution containing the desired compound by a conventional method such as distilling-off of the solvent, solvent extraction, etc., and if necessary, purified by recrystallization, column chromatography, etc., whereby the desired compound can be produced.

Process B (when $R^1$ is a hydrogen atom)

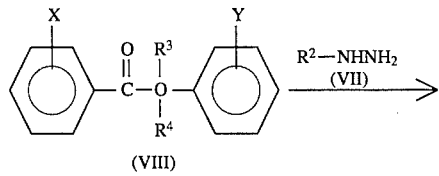
(VIII)

-continued
Process B (when $R^1$ is a hydrogen atom)

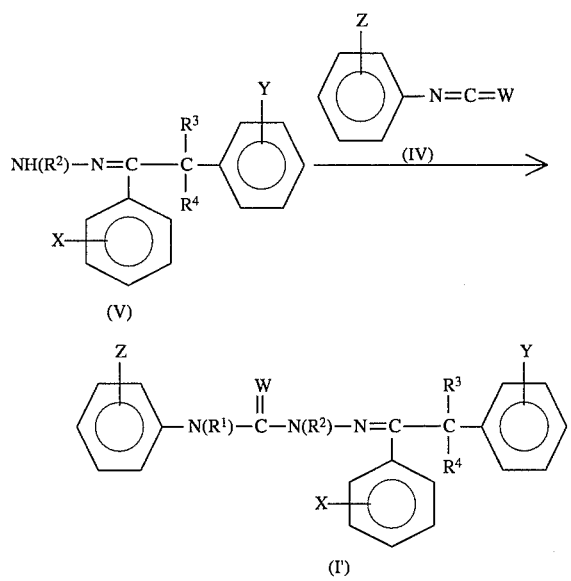
(I')

wherein $R^1$, $R^2$, $R^3$, $R^4$, X, Y, Z and W have the same meanings as those defined above, except that $R^1$ is not a lower alkyl group.

A hydrazinecarboxamide derivative of the general formula (I') can be produced by reacting a compound of the general formula (VIII) with a hydrazine derivative of the general formula (VII) in the presence of an inert solvent and in the presence or absence of a catalyst to obtain a compound of the general formula (V), and reacting the compound (V) with a compound of the general formula (IV) in the presence of an inert solvent and in the presence or absence of a catalyst after or without isolating the compound (V).

Reaction B-1.

General formula (VIII)→general formula (V)

As the inert solvent used in this reaction, there can be used the inert solvents exemplified for reaction A-1.

The kind and amount of the catalyst used in this reaction may be the same as in reaction A-1.

The hydrazine derivative of the general formula (VII) used in this reaction may be used in the form of either any of various salts or an aqueous solution having a suitable concentration.

As to the amount of the hydrazine derivative of the general formula (VII) used, the hydrazine derivative can be used in an amount equimolar with or larger than the amount of the compound of the general formula (VIII). Preferably, the amount is properly chosen in the range of 2 to 10 moles per mole of the compound of the general formula (VIII).

The reaction temperature may be properly chosen in the range of room temperature to the boiling range of the inert solvent used. The reaction is carried out preferably at 70° to 80° C.

Although the reaction time is varied depending on the degree of reaction, the reaction temperature and the like, it may be chosen in the range of several minutes to 48 hours.

After completion of the reaction, the desired compound is isolated from a reaction solution containing the desired compound by a conventional method such as distilling-off of the solvent, solvent extraction, etc., and if necessary, purified by recrystallization, column chromatography, etc., whereby the desired compound can be produced.

The compound of the general formula (V) obtained by the reaction may be subjected to the subsequent reaction either after isolation and purification by the above method, or without isolation.

Typical examples of the compound of the general formula (V) obtained by the present production process are listed in Table 1.

General formula (V)

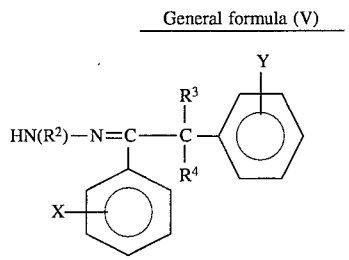

TABLE 1

| No. | $R^2$ | $R^3$ | $R^4$ | X | Y | Physical properties |
|---|---|---|---|---|---|---|
| V-1 | H | H | H | H | H | mp. 55° C. |
| V-2 | H | H | H | H | 4-F | paste |
| V-3 | H | H | H | H | 4-CN | mp. 91° C. |
| V-4 | H | H | H | H | 4-$NO_2$ | mp. 72° C. |
| V-5 | H | H | H | 4-F | 4-F | paste |
| V-6 | H | OH | H | H | H | paste |
| V-7 | $CH_3$ | H | H | H | H | paste |
| V-8 | $CH_3$ | H | H | 3-Cl | 4-CN | paste |
| V-9 | H | OH | H | H | 4-Cl | paste |
| V-10 | H | OH | H | 4-$N(CH_3)_2$ | H | paste |
| V-11 | H | OH | H | 3-Cl | 3-Cl | paste |
| V-12 | H | OH | H | 4-$CH_3$ | 4-$CH_3$ | paste |
| V-13 | H | $CH_3$ | H | H | H | paste |
| V-14 | H | $OCH_3$ | H | H | H | paste |
| V-15 | H | H | H | 3-Cl | 4-CN | paste |
| V-16 | H | H | H | 3-F | 4-CN | paste |
| V-17 | H | H | H | 3-Br | 4-CN | paste |
| V-18 | H | H | H | 3-$CF_3$ | 4-CN | paste |

Table 2 shows $^1$-NMR data of the compounds having physical properties as paste listed in Table 1.

TABLE 2

| No. | $^1$H-NMR($CDCl_3$/TMS, δ value, ppm.) |
|---|---|
| V-2 | 3.74+3.95(s, 2H), 5.13+5.33(bs, 2H), 6.37–7.76(m, 9H). (Mixture of E- and Z-forms) |
| V-5 | 3.72+3.98(s, 2H), 5.10+5.37(bs, 2H), 6.85–7.69(m, 8H). (Mixture of E- and Z-forms) |
| V-6 | 4.73(bs, 1H), 5.18(bs, 2H), 5.31(s, 1H), 6.71–7.58(m, 10H). |
| V-7 | 2.98(s, 3H), 3.95(s, 2H), 5.00(bs, 1H), 6.90–7.81(m, 10H). |
| V-8 | 3.06(s, 3H), 4.00(s, 2H), 5.08(bs, 1H), 7.22–7.69(m, 8H). |
| V-9 | 4.91(bs, 1H), 5.29(bs, 2H), 5.37(bs, 1H), 6.85–7.45(m, 9H). |
| V-10 | 2.96(s, 6H), 4.96(bs, 1H), 5.31(bs, 2H), 5.39(bs, 1H), 6.60–7.25(m, 9H). |
| V-11 | 4.73(bs, 1H), 5.32(bs, 2H), 6.18(bs, 1H), 6.81–7.12(m, 8H). |
| V-12 | 2.27(s, 3H), 2.31(s, 3H), 4.81(bs, 1H), 5.25(bs, 2H), 5.86(bs, 1H), 6.86–7.52(m, 8H). |
| V-13 | 1.50(d, 3H), 3.95(q, 1H), 4.98(bs, 2H), 6.77–7.52(m, 10H). |
| V-15 | 3.82+4.06(s, 2H), 5.23+5.51(bs, 2H), 6.96–7.85(m, 8H). (Mixture of E- and Z-forms) |
| V-16 | 3.81+4.03(s, 2H), 5.26+5.55(bs, 2H), 6.81–7.62(m, 8H), (Mixture of E- and Z-forms) |
| V-17 | 3.81+4.04(s, 2H), 5.22+5.51(bs, 2H), |

TABLE 2-continued

| No. | $^1$H-NMR($CDCl_3$/TMS, δ value, ppm.) |
|---|---|
| | 7.00–7.85(m, 8H). (Mixture of E- and Z-forms) |
| V-18 | 3.84+4.10(s, 2H), 5.21+5.58(bs, 2H), 7.24+7.96(m, 8H). (Mixture of E- and Z-forms) |

Reaction B-2.

General formula (V)→general formula (I')

As the inert solvent used in this reaction, there can be used, for example, the inert solvents usable in reaction A-1 except for the alcohols, the carboxylic acids and water. There can also be used esters such as ethyl acetate and the like and pyridines.

As the catalyst used in this reaction, there can be used, for example, amines such as triethylamine and the like. The amount of the catalyst used may be properly chosen in the range of catalytic amount to a number of moles larger than that of the compound of the general formula (V).

Although the reactants are used in equimolar amount because the reaction is an equimolar reaction, either of them may be used in excess.

The reaction temperature may be properly chosen in the range of −20° C. to the boiling range of the inert solvent used, and is preferably in the range of −10° C. to room temperature.

Although the reaction time is varied depending on the degree of reaction, the reaction temperature and the like, it may be chosen in the range of several minutes to 48 hours.

After completion of the reaction, the same treatment as in the case of reaction B-1 is carried out, whereby the desired compound can be produced.

Process C

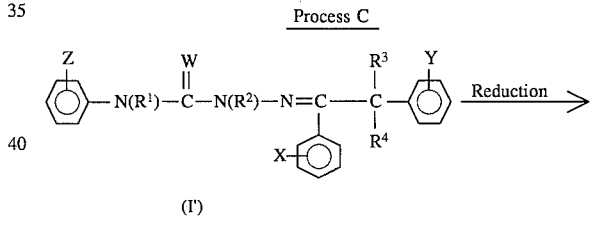

(I')

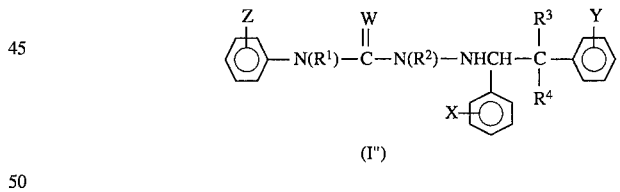

(I")

wherein $R^1$, $R^2$, $R^3$, $R^4$, X, Y, Z and W have the same meanings as those defined above.

A hydrazinecarboxamide derivative of the general formula (I") can be produced by reducing a hydrazinecarboxamide derivative of the general formula (I') with a reducing agent or by catalytic hydrogenation in the presence or absence of an inert solvent.

Reaction C-1.

General formula (I')→general formula (I")

This reduction reaction can be carried out by the use of a suitable reducing agent, or it can be carried out as catalytic hydrogenation in the presence of a suitable catalyst.

As the reducing agent, there can be used, for example, metal hydrides such as $LiAlH_4$, $NaBH_3CN$, $LiBH_3CN$, etc. and reducing agents such as $NaHSO_3$ and the like. The amount of the reducing agent used may be chosen so that its number of moles in terms of the number of moles of hydride as reducing agent may be equal to or larger than that of the hydrazinecarboxamide derivative of the general formula (I').

As the inert solvent used in the reaction, any inert solvent may be used so long as it does not markedly inhibit the progress of the reaction. There can be exemplified alcohols such as methanol, ethanol, propanol, butanol, etc.; ethers such as diethyl ether, diglyme, dioxane, tetrahydrofuran, etc., Cellosolves such as Methyl Cellosolve, etc.; dimethylformamide; dimethylacetamide; dimethyl sulfoxide; sulfolane; and water.

These inert solvents may be used singly or as a mixture thereof.

The reaction is carried out under acidic or neutral conditions in the pH range of 1 to 7. The pH is preferably in the range of 4 to 6 and is adjusted by adding hydrogen chloride, hydrogen bromide or the like to the reaction system.

The reaction temperature may be properly chosen in the range of −20° C. to the boiling range of the inert solvent used.

Although the reaction time is varied depending of the scale of reaction, the reaction temperature and the like, it is several minutes to 48 hours.

After completion of the reaction, the desired compound is isolated from a reaction solution containing the desired product by a conventional method such as distilling-off of the solvent, solvent extraction, etc., and if necessary, purified by recrystallization, column chromatography, etc., whereby the desired compound can be produced.

When catalytic hydrogenation is carried out as the reduction reaction, it is carried out according to, for example, the conventional method described in Shin Jikken Kagaku Koza, Vol. 15-11, Maruzen Co., Ltd., etc. As the solvent usable in this case, there can be exemplified alcohols such as methanol, ethanol, propanol, butanol, etc.; Cellosolves such as Methyl Cellosolve, etc.; ethers such as diethyl ether, diglyme, dioxane, tetrahydrofuran, etc.; hydrocarbons such as hexane, cyclohexane, etc.; fatty acids or esters thereof, such as acetic acid, ethyl acetate, etc.; amides such as dimethylformamide, dimethylacetamide, N-methylpyrrolidone, etc.; and ureas such as dimethylimidazoline, tetramethylurea, etc.

These inert solvents may be used singly or as a mixture thereof.

As the catalyst used in the reaction, there can be used typical catalysts for catalytic hydrogenation, for example, palladium-carbon, palladium black, platinum dioxide and Raney nickel. The amount of the catalyst used may be properly chosen in the range of 0.0001 to 20% by weight based on the weight of the hydrazinecarboxamide derivative of the general formula (I').

The hydrogen pressure in the reaction can be chosen in the range of atmospheric pressure to 300 atmospheres and is preferably in the range of atmospheric pressure to 50 atmospheres.

The reaction temperature may be properly chosen in the range of room temperature to the boiling range of the inert solvent used and is preferably in the range of room temperature to 80° C.

Although the reaction time is varied depending on the scale of reaction, the reaction temperature and the like, it is several minutes to 80 hours.

After completion of the reaction, a reaction solution containing the desired compound is treated in the same manner as in the case of using the reducing agent, whereby the desired compound can be produced.

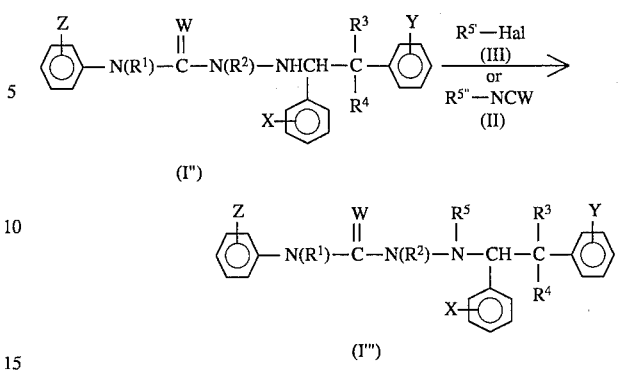

Process D wherein $R^1$, $R^2$, $R^3$, $R^4$, $R^5$, X, Y and Z have the same meanings as those defined above $R^{5'}$, is a lower alkylcarbonyl group, a lower haloalkylcarbonyl group, a cycloalkylcarbonyl group, a lower alkoxycarbonyl group, a lower alkoxydicarbonyl group, an unsubstituted phenylcarbonyl group, or a substituted phenylcarbonyl group having 1 to 5 substituents which may be the same or different and are selected from the group consisting of a halogen atoms, lower alkyl groups, lower haloalkyl groups, lower alkoxy groups and lower haloalkoxy groups, $R^{5''}$ is a lower alkyl group, an unsubstituted phenyl group, or a substituted phenyl group having 1 to 5 substituents which may be the same or different and are selected from the group consisting of halogen atoms, lower alkyl groups, lower haloalkyl groups, lower alkoxy groups and lower haloalkoxy groups and Hal is a halogen atom.

A hydrazinecarboxamide derivative of the general formula (I''') can be produced by reacting a hydrazinecarboxamide derivative of the general formula (I'') with a halide of the general formula (III) or an isocyanate of the general formula (II) in the presence of an inert solvent and a base.

Reaction D-1.

General formula (I'')→general formula (I''')

As the inert solvent used in this reaction, any inert solvent may be used so long as it does not markedly inhibit the progress of the reaction. There can be exemplified halogenated hydrocarbons such as methylene chloride, chloroform, carbon tetrachloride, etc.; aromatic hydrocarbons such as benzene, toluene, xylene, etc.; esters such as ethyl acetate, etc.; nitriles such as acetonitrile, benzonitrile, etc.; ethers such as Methyl Cellosolve, diethyl ether, diglyme, dioxane, tetrahydrofuran, etc.; sulfolane; and dimethylsulfoxide. The inert solvents may be used singly or as a mixture thereof.

As the base used in the reaction, inorganic based or organic bases can be used. As the inorganic bases, there can be exemplified hydroxides, carbonates and alcoholates of alkali metals or alkaline earth metals, for example, sodium, potassium, magnesium and calcium. As the organic bases, triethylamine and pyridine can be exemplified.

Although the reactants are used in equimolar amount because the reaction is an equimolar reaction, either of them may be used in excess.

The reaction temperature may be chosen in the range of 0° C. to the boiling range of the inert solvent used.

Although the reaction time is varied depending on the scale of reaction, the reaction temperature and the like, it may be chosen in the range of several minutes to 48 hours.

After completion of the reaction, the desired compound is isolated from a reaction solution containing the desired compound by a conventional method and if necessary, purified by recrystallization, column chromatography, etc., whereby the desired compound can be produced.

Typical examples of the hydrazinecarboxamide derivative of the general formula (I) of the present invention are given below but they are not intended in any way to limit the scope of the present invention.
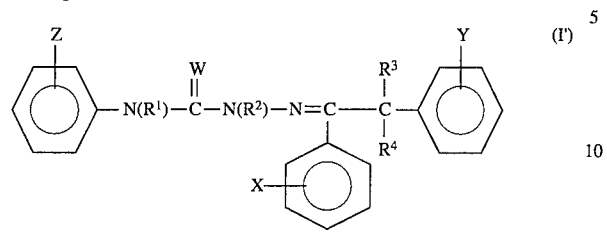

TABLE 3

| No. | R¹ | R² | R³ | R⁴ | X | Y | Z | W | Physical properties |
|---|---|---|---|---|---|---|---|---|---|
| A001 | H | H | H | H | H | H | H | O | m.p. 181° C. |
| A002 | H | H | H | H | H | H | 2-Cl | O | m.p. 197° C. |
| A003 | H | H | H | H | H | H | 3-Cl | O | m.p. 188° C. |
| A004 | H | H | H | H | H | H | 4-Cl | O | m.p. 199° C. |
| A005 | H | H | H | H | H | H | 4-OCH₃ | O | m.p. 144° C. |
| A006 | H | H | H | H | H | H | 4-OCHF₂ | O | m.p. 172° C. |
| A007 | H | H | H | H | H | H | 4-OCF₃ | O | m.p. 149° C. |
| A008 | H | H | H | H | H | 4-OH | 4-CF₃ | O | m.p. 206° C. |
| A009 | H | H | H | H | H | 4-OH | 4-OCF₃ | O | m.p. 211° C. |
| A010 | H | H | H | H | H | 4-OH | 4-Cl | O | m.p. 192° C. |
| A011 | H | H | H | H | H | 2-Cl | 4-Cl | O | m.p. 224° C. |
| A012 | H | H | H | H | H | 2-Cl | 4-OCF₃ | O | m.p. 227° C. |
| A013 | H | H | H | H | H | 2-Cl | 4-Cl | O | m.p. 204° C. |
| A014 | H | H | H | H | H | 3-Cl | 4-CF₃ | O | m.p. 203° C. |
| A015 | H | H | H | H | H | 3-Cl | 4-OCF₃ | O | m.p. 209° C. |
| A016 | H | H | H | H | H | 3-Cl | 4-Cl | O | m.p. 191° C. |
| A017 | H | H | H | H | H | 4-Cl | 4-CF₃ | O | m.p. 206° C. |
| A018 | H | H | H | H | H | 4-Cl | 4-CF₃ | O | m.p. 193° C. |
| A019 | H | H | H | H | H | 4-Cl | 4-OC₄H₇-t | O | m.p. 186° C. |
| A020 | H | H | H | H | H | 4-Cl | 4-OCF₂CHF₂ | O | m.p. 197° C. |
| A021 | H | H | H | H | H | 4-Cl | 4-OCF₂CHF₂ | O | m.p. 217° C. |
| A022 | H | H | H | H | H | 4-Cl | 4-O-⌬-CF₃ | O | m.p. 209° C. |
| A023 | H | H | H | H | H | 2,4-Cl₂ | 4-Cl | O | m.p. 202° C. |
| A024 | H | H | H | H | H | 2,4-Cl₂ | 4-CF₃ | O | m.p. 219° C. |
| A025 | H | H | H | H | H | 2,4-Cl₂ | 4-OCF₃ | O | m.p. 201° C. |
| A026 | H | H | H | H | H | 4-Br | 4-Cl | O | m.p. 222° C. |
| A027 | H | H | H | H | H | 4-Br | 4-CF₃ | O | m.p. 202° C. |
| A028 | H | H | H | H | H | 4-Br | 4-OCF₃ | O | m.p. 208° C. |
| A029 | H | H | H | H | H | 4-F | 4-Cl | O | m.p. 213° C. |
| A030 | H | H | H | H | H | 4-F | 4-CF₃ | O | m.p. 205° C. |
| A031 | H | H | H | H | H | 3-CN | 4-OCF₃ | O | m.p. 187° C. |
| A032 | H | H | H | H | H | 3-CN | 4-Cl | O | m.p. 192° C. |
| A033 | H | H | H | H | H | 3-CN | 4-OCF₃ | O | m.p. 181° C. |
| A034 | H | H | H | H | H | 4-CN | 4-OCF₃ | O | m.p. 195° C. |
| A035 | H | H | H | H | H | 4-CN | H | O | m.p. 209° C. |
| A036 | H | H | H | H | H | 4-CN | 2-Cl | O | m.p. 116° C. |
| A037 | H | H | H | H | H | 4-CN | 3-Cl | O | m.p. 180° C. |
| A038 | H | H | H | H | H | 4-CN | 4-Cl | O | m.p. 217° C. |
| A039 | H | H | H | H | H | 4-CN | 4-Cl | S | m.p. 128° C. |
| A040 | H | H | H | H | H | 4-CN | 3,4-Cl₂ | O | m.p. 230° C. |
| A041 | H | H | H | H | H | 4-CN | 3,5-Cl₂ | O | m.p. 205° C. |
| A042 | H | H | H | H | H | 4-CN | 4-Br | O | m.p. 208° C. |

TABLE 3-continued

| No. | R¹ | R² | R³ | R⁴ | X | Y | Z | W | Physical properties |
|---|---|---|---|---|---|---|---|---|---|
| A043 | H | H | H | H | H | 4-CN | 3-F | O | m.p. 200° C. |
| A044 | H | H | H | H | H | 4-CN | 4-F | O | m.p. 207° C. |
| A045 | H | H | H | H | H | 4-CN | 4-CN | S | m.p. 195° C. |
| A046 | H | H | H | H | H | 4-CN | 4-NO₂ | O | m.p. 231° C. |
| A047 | H | H | H | H | H | 4-CN | 4-CH₃ | O | m.p. 215° C. |
| A048 | H | H | H | H | H | 4-CN | 4-C₄H₇-t | O | m.p. 213° C. |
| A049 | H | H | H | H | H | 4-CN | 3-CF₃ | O | m.p. 193° C. |
| A050 | H | H | H | H | H | 4-CN | 4-CF₃ | O | m.p. 217° C. |
| A051 | H | H | H | H | H | 4-CN | 4-OCF₃ | S | m.p. 116° C. |
| A052 | H | H | H | H | H | 4-CN | 4-OCH₃ | O | m.p. 204° C. |
| A053 | H | H | H | H | H | 4-CN | 4-OC₄H₇-t | O | m.p. 204° C. |
| A054 | H | H | H | H | H | 4-CN | 4-OCHF₂ | S | m.p. 197° C. |
| A055 | H | H | H | H | H | 4-CN | 4-OCHF₂ | O | Paste |
| A056 | H | H | H | H | H | 4-CN | 4-OCF₃ | O | m.p. 214° C. E-form |
| A057 | H | H | H | H | H | 4-CN | 4-OCF₃ | O | m.p. 159° C. Z-form |
| A058 | H | H | H | H | H | 4-CN | 4-OCH₂CF₃ | O | m.p. 221° C. |
| A059 | H | H | H | H | H | 4-CN | 4-OCF₂CHF₂ | O | m.p. 193° C. |
| A060 | H | H | H | H | H | 4-CN | 4-O-C₆H₅ | O | m.p. 206° C. |
| A061 | H | H | H | H | H | 4-CN | 4-O-C₆H₄-4-CF₃ | O | m.p. 182° C. |
| A062 | H | H | H | H | H | 4-CN | 4-O-(3-Cl,4-CF₃)C₆H₃ | O | m.p. 215° C. |
| A063 | H | H | H | H | H | 4-CN | 4-O-(4-CF₃)pyridyl | O | m.p. 167° C. |
| A064 | H | H | H | H | H | 4-CN | 4-O-(3-Cl,4-CF₃)pyridyl | O | m.p. 216° C. |

TABLE 3-continued

| No. | R¹ | R² | R³ | R⁴ | X | Y | Z | W | Physical properties |
|---|---|---|---|---|---|---|---|---|---|
| A065 | H | H | H | H | H | 4-CN | 3,5-Cl₂-4-O-C₆H₃-CF₃ (4-CF₃) | O | m.p. 228° C. |
| A066 | H | H | H | H | H | 4-CN | 3,5-Cl₂-4-O-(2-Cl,4-CF₃-C₆H₃) | O | m.p. 140° C. |
| A067 | H | H | H | H | H | 4-CN | 4-COOCH₃ | O | m.p. 230° C. |
| A068 | H | H | H | H | H | 2-NO₂ | 4-CF₃ | O | m.p. 203° C. |
| A069 | H | H | H | H | H | 2-NO₂ | 4-OCF₃ | O | m.p. 195° C. |
| A070 | H | H | H | H | H | 4-NO₂ | H | O | m.p. 194° C. |
| A071 | H | H | H | H | H | 4-NO₂ | 2-Cl | O | m.p. 220° C. |
| A072 | H | H | H | H | H | 4-NO₂ | 3-Cl | O | m.p. 182° C. |
| A073 | H | H | H | H | H | 4-NO₂ | 4-Cl | O | m.p. 222° C. |
| A074 | H | H | H | H | H | 4-NO₂ | 4-Cl | O | m.p. 206° C. |
| A075 | H | H | H | H | H | 4-NO₂ | 4-F | O | m.p. 206° C. |
| A076 | H | H | H | H | H | 4-NO₂ | 3-CF₃ | O | m.p. 197° C. |
| A077 | H | H | H | H | H | 4-NO₂ | 4-CF₃ | O | m.p. 205° C. |
| A078 | H | H | H | H | H | 4-NO₂ | 4-OCHF₂ | O | m.p. 209° C. |
| A079 | H | H | H | H | H | 4-NO₂ | 4-OCF₃ | O | m.p. 189° C. |
| A080 | H | H | H | H | H | 4-NO₂ | 4-OCF₃ | S | m.p. 139° C. |
| A081 | H | H | H | H | H | 4-NO₂ | 4-OCF₂CHF₂ | O | m.p. 191° C. |
| A082 | H | H | H | H | H | 4-NO₂ | 4-SCF₃ | O | m.p. 200° C. |
| A083 | H | H | H | H | H | 4-NO₂ | 4-Cl | S | m.p. 204° C. |
| A084 | H | H | H | H | H | 4-CH₃ | 4-F | O | m.p. 192° C. |
| A085 | H | H | H | H | H | 4-CH₃ | 3-CF₃ | O | m.p. 205° C. |
| A086 | H | H | H | H | H | 4-CH₃ | 4-CF₃ | O | m.p. 204° C. |
| A087 | H | H | H | H | H | 4-CH₃ | 4-OCF₃ | O | m.p. 186° C. |
| A088 | H | H | H | H | H | 4-OCH₃ | 4-Cl | O | m.p. 191° C. |
| A089 | H | H | H | H | H | 4-OCH₃ | 4-CF₃ | O | m.p. 198° C. |
| A090 | H | H | H | H | H | 4-OCH₃ | 4-OCF₃ | O | m.p. 183° C. |
| A091 | H | H | H | H | H | 4-OCHF₂ | 4-OCF₃ | O | m.p. 162° C. |
| A092 | H | H | H | H | H | 4-OCF₂CHF₂ | 4-CF₃ | O | m.p. 161° C. |
| A093 | H | H | H | H | H | 4-OCF₂CHF₂ | 4-OCF₃ | O | m.p. 185° C. |
| A094 | H | H | H | H | H | 4-OCH₂CH=CH₂ | 4-OCF₂CHF₂ | O | m.p. 168° C. |
| A095 | H | H | H | H | H | 4-O—COCH₃ | 4-OCF₃ | O | m.p. 174° C. |
| A096 | H | H | H | H | H | 4-OSO₂CH₃ | 4-OCF₃ | O | m.p. 171° C. |
| A097 | H | H | H | H | H | 4-OSO₂CF₃ | 4-CF₃ | O | m.p. 175° C. |
| A098 | H | H | H | H | H | 4-SCH₃ | 4-OCF₃ | O | m.p. 189° C. |
| A099 | H | H | H | H | H | 4-SCH₃ | 3-CH₃ | O | m.p. 171° C. |
| A100 | H | H | H | H | H | 4-SOCH₃ | 4-OCF₃ | O | m.p. 195° C. |
| A101 | H | H | H | H | H | 4-SOCH₃ | 4-OCF₃ | O | m.p. 192° C. |
| A102 | H | H | H | H | H | 4-SO₂CH₃ | 4-Cl | O | m.p. 210° C. |

TABLE 3-continued

| No. | R¹ | R² | R³ | R⁴ | X | Y | Z | W | Physical properties |
|---|---|---|---|---|---|---|---|---|---|
| A103 | H | H | H | H | H | 4-SO$_2$CH$_3$ | 4-OCF$_3$ | O | m.p. 196° C. |
| A104 | H | H | H | H | H | 4-NH$_2$ | 4-OCF$_3$ | O | m.p. 148° C. |
| A105 | H | H | H | H | H | 4-NHCOCH$_3$ | 4-OCF$_3$ | O | m.p. 206° C. |
| A106 | H | H | H | H | H | 4-NHSO$_2$CH$_3$ | 4-OCF$_3$ | O | m.p. 210° C. |
| A107 | H | H | H | H | 2-Cl | H | 4-Cl | O | m.p. 171° C. |
| A108 | H | H | H | H | 2-Cl | H | 4-CF$_3$ | O | m.p. 177° C. |
| A109 | H | H | H | H | 2-Cl | H | 4-OCF$_3$ | O | m.p. 166° C. |
| A110 | H | H | H | H | 3-Cl | H | 4-CF$_3$ | O | m.p. 226° C. |
| A111 | H | H | H | H | 3-Cl | H | 4-OCF$_3$ | O | m.p. 212° C. |
| A112 | H | H | H | H | 3-Cl | 4-Cl | 4-CF$_3$ | O | m.p. 207° C. |
| A113 | H | H | H | H | 3-Cl | 4-Cl | 4-OCF$_3$ | O | m.p. 201° C. |
| A114 | H | H | H | H | 3-Cl | 4-F | 4-Cl | O | m.p. 207° C. |
| A115 | H | H | H | H | 3-Cl | 4-F | 4-CF$_3$ | O | m.p. 195° C. |
| A116 | H | H | H | H | 3-Cl | 4-F | 4-OCF$_3$ | O | m.p. 183° C. |
| A117 | H | H | H | H | 3-Cl | 4-CN | 2,3,4,5,6-F$_5$ | O | m.p. 206° C. |
| A118 | H | H | H | H | 3-Cl | 4-CN | 4-Cl | O | m.p. 218° C. |
| A119 | H | H | H | H | 3-Cl | 4-CN | 2,3-Cl$_2$ | O | m.p. 218° C. |
| A120 | H | H | H | H | 3-Cl | 4-CN | 2,4-Cl$_2$ | O | m.p. 221° C. |
| A121 | H | H | H | H | 3-Cl | 4-CN | 2,5-Cl$_2$ | O | m.p. 186° C. |
| A122 | H | H | H | H | 3-Cl | 4-CN | 2,6-Cl$_2$ | O | m.p. 233° C. |
| A123 | H | H | H | H | 3-Cl | 4-CN | 3,4-Cl$_2$ | O | m.p. 215° C. |
| A124 | H | H | H | H | 3-Cl | 4-CN | 3,5-Cl$_2$ | O | m.p. 197° C. |
| A125 | H | H | H | H | 3-Cl | 4-CN | 4-Br | O | m.p. 226° C. |
| A126 | H | H | H | H | 3-Cl | 4-CN | 4-C$_4$H$_9$-t | O | m.p. 207° C. |
| A127 | H | H | H | H | 3-Cl | 4-CN | 4-CF$_3$ | O | m.p. 189° C. |
| A128 | H | H | H | H | 3-Cl | 4-CN | 4-OCH$_3$ | O | m.p. 198° C. |
| A129 | H | H | H | H | 3-Cl | 4-CN | 4-OC$_4$H$_9$-t | O | m.p. 167° C. |
| A130 | H | H | H | H | 3-Cl | 4-CN | 4-OCHF$_2$ | S | m.p. 187° C. |
| A131 | H | H | H | H | 3-Cl | 4-CN | 4-OCF$_3$ | O | E-form m.p. 148° C. Z-form m.p. 199° C. |
| A132 | H | H | H | H | 3-Cl | 4-CN | 4-OCF$_3$ | S | m.p. 226° C. |
| A133 | H | H | H | H | 3-Cl | 4-CN | 4-OCH$_2$CF$_3$ | O | m.p. 184° C. |
| A134 | H | H | H | H | 3-Cl | 4-CN | 4-OCF$_2$CHF$_2$ | O | m.p. 207° C. |
| A135 | H | H | H | H | 3-Cl | 4-CN | 3,5-Cl$_2$,4-OCF$_2$CHF$_2$ | O | m.p. 196° C. |
| A137 | H | H | H | H | 3-Cl | 4-CN | 4-OCF$_2$CHClF | O | m.p. 184° C. |
| A138 | H | H | H | H | 3-Cl | 4-CN | 4-OCF$_2$CHFCF$_3$ | O |  |
| A139 | H | H | H | H | 3-Cl | 4-CN | 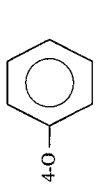 | O | m.p. 201° C. |
| A140 | H | H | H | H | 3-Cl | 4-CN | 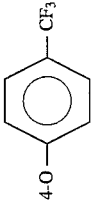 | O | m.p. 198° C. |

TABLE 3-continued

| No. | R¹ | R² | R³ | R⁴ | X | Y | Z | W | Physical properties |
|---|---|---|---|---|---|---|---|---|---|
| A141 | H | H | H | H | 3-Cl | 4-CN | 4-O-(3-Cl-4-CF₃-phenyl) | O | m.p. 216° C. |
| A142 | H | H | H | H | 3-Cl | 4-CN | 4-O-(4-CF₃-pyridin-2-yl) | O | m.p. 196° C. |
| A143 | H | H | H | H | 3-Cl | 4-CN | 4-O-(3-Cl-5-CF₃-pyridin-2-yl) | O | m.p. 223° C. |
| A144 | H | H | H | H | 3-Cl | 4-CN | 3,5-Cl₂-4-O-(4-CF₃-phenyl) | O | m.p. 206° C. |
| A145 | H | H | H | H | 3-Cl | 4-CN | 3,5-Cl₂-4-O-(3-Cl-4-CF₃-phenyl) | O | m.p. 145° C. |
| A146 | H | H | H | H | 3-Cl | 4-CN | 4-SCH₃ | O | m.p. 194° C. |
| A147 | H | H | H | H | 3-Cl | 4-CN | 4-SCF₃ | O | m.p. 215° C. |
| A148 | H | H | H | H | 3-Cl | 4-CN | 4-SCHF₂ | O | m.p. 195° C. |
| A149 | H | H | H | H | 3-Cl | 4-CN | 4-SCF₂CHF₂ | O | m.p. 221° C. |
| A150 | H | H | H | H | 3-Cl | 4-CN | 4-SOCH₃ | O | m.p. 216° C. |
| A151 | H | H | H | H | 3-Cl | 4-CN | 4-SOCF₃ | O | m.p. 205° C. |
| A152 | H | H | H | H | 3-Cl | 4-CN | 4-SOCF₂CH₃ | O | m.p. 217° C. |
| A153 | H | H | H | H | 3-Cl | 4-CN | 4-SO₂CH₃ | O | m.p. 253° C. |
| A154 | H | H | H | H | 3-Cl | 4-CN | 4-SO₂CHF₂ | O | m.p. 212° C. |
| A155 | H | H | H | H | 3-Cl | 4-CN | 4-SO₂CF₃ | O | m.p. 212° C. |
| A156 | H | H | H | H | 3-Cl | 4-CN | 4-SO₂CF₂CHF₂ | O | m.p. 216° C. |
| A157 | H | H | H | H | 3-Cl | 4-CN | 4-COOCH₃ | O | m.p. 211° C. |
| A158 | H | H | H | H | 4-Cl | H | 4-CF₃ | O | m.p. 192° C. |
| A159 | H | H | H | H | 4-Cl | H | 4-OCF₃ | O | m.p. 210° C. |
| A160 | H | H | H | H | 4-Cl | 4-Cl | 4-Cl | O | m.p. 184° C. |
| A161 | H | H | H | H | 4-Cl | 4-Cl | 4-CF₃ | O | |

TABLE 3-continued

| No. | R¹ | R² | R³ | R⁴ | X | Y | Z | W | Physical properties |
|---|---|---|---|---|---|---|---|---|---|
| A162 | H | H | H | H | 4-Cl | 4-Cl | 4-OCF₃ | O | m.p. 190° C. |
| A163 | H | H | H | H | 4-Cl | 4-F | 4-Cl | O | m.p. 201° C. |
| A164 | H | H | H | H | 4-Cl | 4-F | 4-CF₃ | O | m.p. 195° C. |
| A165 | H | H | H | H | 4-Cl | 4-F | 4-OCF₃ | O | m.p. 174° C. |
| A166 | H | H | H | H | 4-Cl | 4-CN | 4-Cl | O | m.p. 221° C. |
| A167 | H | H | H | H | 4-Cl | 4-CN | 4-CF₃ | O | m.p. 216° C. |
| A168 | H | H | H | H | 4-Cl | 4-CN | 4-OCF₃ | S | m.p. 182° C. |
| A169 | H | H | H | H | 4-Cl | 4-CN | 4-OCF₃ | O | m.p. 193° C. |
| A170 | H | H | H | H | 4-Cl | 4-CN | 4-OCF₂CHF₂ | O | m.p. 201° C. |
| A171 | H | H | H | H | 4-Cl | 4-NO₂ | 4-Cl | O | m.p. 217° C. |
| A172 | H | H | H | H | 4-Cl | 4-NO₂ | 4-CF₃ | O | m.p. 213° C. |
| A173 | H | H | H | H | 4-Cl | 4-NO₂ | 4-OCF₃ | O | m.p. 206° C. |
| A174 | H | H | H | H | 3,4-Cl₂ | H | 4-Cl | O | m.p. 212° C. |
| A175 | H | H | H | H | 3,4-Cl₂ | H | 4-CF₃ | O | m.p. 206° C. |
| A176 | H | H | H | H | 3,4-Cl₂ | H | 4-OCF₃ | O | m.p. 193° C. |
| A177 | H | H | H | H | 3,4-Cl₂ | 4-CN | 4-Cl | O | m.p. 226° C. |
| A178 | H | H | H | H | 3,4-Cl₂ | 4-CN | 4-CF₃ | O | m.p. 212° C. |
| A179 | H | H | H | H | 3,4-Cl₂ | 4-CN | 4-OCF₃ | O | m.p. 193° C. |
| A180 | H | H | H | H | 3,5-Cl₂ | H | 4-Cl | O | m.p. 239° C. |
| A181 | H | H | H | H | 3,5-Cl₂ | H | 4-CF₃ | O | m.p. 227° C. |
| A182 | H | H | H | H | 3,5-Cl₂ | H | 4-OCF₃ | O | m.p. 228° C. |
| A183 | H | H | H | H | 3,5-Cl₂ | 4-CN | 4-Cl | O | m.p. 213° C. |
| A184 | H | H | H | H | 3,5-Cl₂ | 4-CN | 4-CF₃ | O | m.p. 206° C. |
| A185 | H | H | H | H | 3,5-Cl₂ | 4-CN | 4-OCF₃ | O | m.p. 191° C. |
| A186 | H | H | H | H | 3-Br | H | 4-Cl | O | m.p. 228° C. |
| A187 | H | H | H | H | 3-Br | H | 4-CF₃ | O | m.p. 209° C. |
| A188 | H | H | H | H | 3-Br | H | 4-OCF₃ | O | m.p. 205° C. |
| A189 | H | H | H | H | 3-Br | 4-CN | 4-Cl | O | m.p. 223° C. |
| A190 | H | H | H | H | 3-Br | 4-CN | 2,3-Cl₂ | O | m.p. 233° C. |
| A191 | H | H | H | H | 3-Br | 4-CN | 2,4-Cl₂ | O | m.p. 194° C. |
| A192 | H | H | H | H | 3-Br | 4-CN | 2,6-Cl₂ | O | m.p. 220° C. |
| A193 | H | H | H | H | 3-Br | 4-CN | 3,4-Cl₂ | O | m.p. 197° C. |
| A194 | H | H | H | H | 3-Br | 4-CN | 4-CF₃ | O | m.p. 176° C. |
| A195 | H | H | H | H | 3-Br | 4-CN | 4-OCF₃ | O | m.p. 183° C. |
| A196 | H | H | H | H | 3-Br | 4-CN | 4-OCF₂CHF₂ | O | m.p. 186° C. |
| A197 | H | H | H | H | 3-Br | 4-CN | 4-OCF₂CHClF | O | m.p. 188° C. |
| A198 | H | H | H | H | 3-Br | 4-CN | 4-OCF₂CHFCF₃ | O | m.p. 218° C. |
| A199 | H | H | H | H | 3-Br | 4-CN | 4-SCHF₂ | O | m.p. 206° C. |
| A200 | H | H | H | H | 3-Br | 4-CN | 4-SCF₃ | O | m.p. 221° C. |
| A201 | H | H | H | H | 3-Br | 4-CN | 4-SOCHF₂ | O | m.p. 216° C. |
| A202 | H | H | H | H | 3-Br | 4-CN | 4-SOCF₃ | O | m.p. 193° C. |
| A203 | H | H | H | H | 3-Br | 4-CN | 4-SO₂CHF₂ | O | m.p. 215° C. |
| A204 | H | H | H | H | 3-Br | 4-CN | 4-SO₂CF₃ | O | m.p. 204° C. |
| A205 | H | H | H | H | 4-Br | 3,4-(OCH₃)₂ | 4-Cl | O | m.p. 221° C. |
| A206 | H | H | H | H | 4-Br | 3,4-(OCH₃)₂ | 4-CF₃ | O | m.p. 192° C. |
| A207 | H | H | H | H | 4-Br | 3,4-(OCH₃)₂ | 4-OCF₃ | O | m.p. 197° C. |
| A208 | H | H | H | H | 2-F | H | 4-Cl | O | m.p. 175° C. |
| A209 | H | H | H | H | 2-F | H | 4-CF₃ | O | m.p. 177° C. |
| A210 | H | H | H | H | 2-F | H | 4-OCF₃ | O | m.p. 173° C. |

TABLE 3-continued

| No. | R¹ | R² | R³ | R⁴ | X | Y | Z | W | Physical properties |
|---|---|---|---|---|---|---|---|---|---|
| A211 | H | H | H | H | 2-F | 4-CN | 4-Cl | O | m.p. 180° C. |
| A212 | H | H | H | H | 2-F | 4-CN | 4-CF₃ | O | m.p. 196° C. |
| A213 | H | H | H | H | 2-F | 4-CN | 4-OCF₃ | O | m.p. 170° C. |
| A214 | H | H | H | H | 3-F | H | 4-Cl | O | m.p. 206° C. |
| A215 | H | H | H | H | 3-F | H | 4-CF₃ | O | m.p. 223° C. |
| A216 | H | H | H | H | 3-F | H | 4-OCF₃ | O | m.p. 200° C. |
| A217 | H | H | H | H | 3-F | 4-Cl | 4-CF₃ | O | m.p. 209° C. |
| A218 | H | H | H | H | 3-F | 4-Cl | 4-OCF₃ | O | m.p. 191° C. |
| A219 | H | H | H | H | 3-F | 4-CN | 4-Cl | O | m.p. 208° C. |
| A220 | H | H | H | H | 3-F | 4-CN | 4-CF₃ | O | m.p. 216° C. |
| A221 | H | H | H | H | 3-F | 4-CN | 4-OCF₃ | O | m.p. 202° C. |
| A222 | H | H | H | H | 4-F | H | 4-Cl | O | m.p. 203° C. |
| A223 | H | H | H | H | 4-F | H | 4-OCF₃ | O | m.p. 191° C. |
| A224 | H | H | H | H | 4-F | 4-CN | 4-Cl | O | m.p. 222° C. |
| A225 | H | H | H | H | 4-F | 4-CN | 4-CF₃ | O | m.p. 185° C. |
| A226 | H | H | H | H | 4-F | 4-CN | 4-OCF₃ | O | m.p. 184° C. |
| A227 | H | H | H | H | 4-F | 4-F | 4-CF₃ | O | m.p. 199° C. |
| A228 | H | H | H | H | 4-F | 4-F | 4-OCF₂CHF₂ | O | m.p. 178° C. |
| A229 | H | H | H | H | 4-F | 4-CN | 4-Cl | O | m.p. 187° C. |
| A230 | H | H | H | H | 4-F | 4-CN | 4-CF₃ | O | m.p. 232° C. |
| A231 | H | H | H | H | 4-F | 4-CN | 4-OCF₃ | O | m.p. 202° C. |
| A232 | H | H | H | H | 4-F | 4-NO₂ | 4-Cl | O | m.p. 210° C. |
| A233 | H | H | H | H | 4-F | 4-NO₂ | 4-CF₃ | O | m.p. 209° C. |
| A234 | H | H | H | H | 4-F | 4-NO₂ | 4-CF₃ | O | m.p. 220° C. |
| A235 | H | H | H | H | 4-F | H | 4-OCF₃ | O | m.p. 204° C. |
| A236 | H | H | H | H | 3,5-F₂ | H | 4-Cl | O | m.p. 218° C. |
| A237 | H | H | H | H | 3,5-F₂ | H | 4-CF₃ | O | m.p. 208° C. |
| A238 | H | H | H | H | 3,5-F₂ | H | 4-OCF₃ | O | m.p. 211° C. |
| A239 | H | H | H | H | 3-I | 4-CN | 4-Cl | O | m.p. 213° C. |
| A240 | H | H | H | H | 3-I | 4-CN | 4-CF₃ | O | m.p. 205° C. |
| A241 | H | H | H | H | 3-I | 4-CN | 4-Cl | O | m.p. 201° C. |
| A242 | H | H | H | H | 3-I | 4-CN | 4-OCF₂CHF₂ | O | m.p. 196° C. |
| A243 | H | H | H | H | 2-CH₃ | 4-CN | 4-CF₃ | O | m.p. 121° C. |
| A244 | H | H | H | H | 2-CH₃ | 4-CN | 4-CF₃ | O | m.p. 135° C. |
| A245 | H | H | H | H | 2-CH₃ | 4-CN | 4-Cl | O | m.p. 160° C. |
| A246 | H | H | H | H | 3-CH₃ | H | 4-CF₃ | O | m.p. 185° C. |
| A247 | H | H | H | H | 3-CH₃ | H | 4-CF₃ | O | m.p. 193° C. |
| A248 | H | H | H | H | 3-CH₃ | H | 4-CF₃ | O | m.p. 198° C. |
| A249 | H | H | H | H | 3-CH₃ | 4-CN | 4-Cl | O | m.p. 200° C. |
| A250 | H | H | H | H | 3-CH₃ | 4-CN | 4-CF₃ | O | m.p. 194° C. |
| A251 | H | H | H | H | 3-CH₃ | 4-CN | 4-OCF₃ | O | m.p. 189° C. |
| A252 | H | H | H | H | 4-CH₃ | H | 4-Cl | O | m.p. 206° C. |
| A253 | H | H | H | H | 4-CH₃ | H | 4-OCF₃ | O | m.p. 194° C. |
| A254 | H | H | H | H | 4-C₄H₉-t | 3,4-(OCH₃)₂ | 4-Cl | O | m.p. 122° C. |
| A255 | H | H | H | H | 4-C₄H₉-t | 3,4-(OCH₃)₂ | 4-CF₃ | O | m.p. 202° C. |
| A256 | H | H | H | H | 4-C₄H₉-t | 3,4-(OCH₃)₂ | 4-OCF₃ | O | m.p. 200° C. |
| A257 | H | H | H | H | 3-CF₃ | H | 4-Cl | O | m.p. 206° C. |
| A258 | H | H | H | H | 3-CF₃ | H | 4-CF₃ | O | m.p. 192° C. |
| A259 | H | H | H | H | 3-CF₃ | H | 4-OCF₃ | O | m.p. 210° C. |

TABLE 3-continued

| No. | R¹ | R² | R³ | R⁴ | X | Y | Z | W | Physical properties |
|---|---|---|---|---|---|---|---|---|---|
| A260 | H | H | H | H | 3-CF₃ | 4-CN | 4-CF₃ | O | m.p. 188° C. |
| A261 | H | H | H | H | 3-CF₃ | 4-CN | 4-OCF₃ | O | m.p. 191° C. |
| A262 | H | H | H | H | 3-CF₃ | 4-CN | 4-OCF₃ | S | m.p. 149° C. |
| A263 | H | H | H | H | 3-CF₃ | 4-CN | 4-OCF₂CHF₂ | O | m.p. 183° C. |
| A264 | H | H | H | H | 3-CF₃ | 4-OCHF₂ | 4-OCF₃ | O | m.p. 149° C. |
| A265 | H | H | H | H | 3-CF₃ | 4-OSO₂CH₃ | 4-OCF₃ | O | m.p. 173° C. |
| A266 | H | H | H | H | 3,5-(CF₃)₂ | H | 4-Cl | O | m.p. 233° C. |
| A267 | H | H | H | H | 3,5-(CF₃)₂ | H | 4-CF₃ | O | m.p. 227° C. |
| A268 | H | H | H | H | 3-CN | 4-CN | 4-Cl | O | m.p. 229° C. |
| A269 | H | H | H | H | 3-CN | 4-CN | 4-CF₃ | O | m.p. 224° C. |
| A270 | H | H | H | H | 3-CN | 4-CN | 4-OCF₃ | O | m.p. 218° C. |
| A271 | H | H | H | H | 4-CN | 4-CN | 4-Cl | O | m.p. 246° C. |
| A272 | H | H | H | H | 4-CN | 4-CN | 4-CF₃ | O | m.p. 247° C. |
| A273 | H | H | H | H | 3-OCH₃ | 4-CN | 4-OCF₃ | O | m.p. 238° C. |
| A274 | H | H | H | H | 4-OCH₃ | 4-CN | 4-OCF₃ | O | m.p. 194° C. |
| A275 | H | H | H | H | 4-OCH₃ | H | 4-Cl | O | m.p. 201° C. |
| A276 | H | H | H | H | 4-OCH₃ | H | 4-CF₃ | O | m.p. 217° C. |
| A277 | H | H | H | H | 4-OCH₃ | H | 4-OCF₃ | O | m.p. 210° C. |
| A278 | H | H | H | H | 3-OC₃H₇-i | 4-CN | 4-CF₃ | O | m.p. 177° C. |
| A279 | H | H | H | H | 3-OC₃H₇-i | 4-CN | 4-OCF₃ | O | m.p. 180° C. |
| A280 | H | H | H | H | 3-O-C₆H₅ | 4-CN | 4-Cl | O | m.p. 182° C. |
| A281 | H | H | H | H | 3-O-C₆H₅ | 4-CN | 4-CF₃ | O | m.p. 168° C. |
| A282 | H | H | H | H | 3-O-C₆H₅ | 4-CN | 4-OCF₃ | O | m.p. 171° C. |
| A283 | H | H | H | H | 3-OCHF₂ | H | 4-Cl | O | m.p. 185° C. |
| A284 | H | H | H | H | 3-OCHF₂ | H | 4-OCF₃ | O | m.p. 182° C. |
| A285 | H | H | H | H | 3-OCHF₂ | 4-CN | 4-OCF₃ | O | m.p. 188° C. |
| A286 | H | H | H | H | 4-OCHF₂ | H | 4-Cl | O | m.p. 194° C. |
| A287 | H | H | H | H | 4-OCHF₂ | H | 4-CF₃ | O | m.p. 204° C. |
| A288 | H | H | H | H | 4-OCHF₂ | H | 4-OCF₃ | O | m.p. 202° C. |
| A289 | H | H | H | H | 4-OCHF₂ | H | 4-OCF₂CHF₂ | O | m.p. 213° C. |
| A290 | H | H | H | H | 4-OCHF₂ | H | 4-SCF₃ | O | m.p. 208° C. |
| A291 | H | H | H | H | 4-OCHF₂ | 4-CN | 4-SOCF₃ | O | m.p. 204° C. |
| A292 | H | H | H | H | 4-OCF₂CHF₂ | 4-CN | 4-OCF₂CHF₂ | O | m.p. 175° C. |
| A293 | H | H | H | H | 3-OCH₂O-4 | 4-CN | 4-Cl | O | m.p. 206° C. |
| A294 | H | H | H | H | 3-OCH₂O-4 | 4-CN | 4-CF₃ | O | m.p. 182° C. |

TABLE 3-continued

| No. | R¹ | R² | R³ | R⁴ | X | Y | Z | W | Physical properties |
|---|---|---|---|---|---|---|---|---|---|
| A295 | H | H | H | H | 3-OCH₂O-4 | 4-CN | 4-OCF₃ | O | m.p. 180° C. |
| A296 | H | H | H | H | 2-CH=CHCH=CH-3 | 4-CN | 4-Cl | O | m.p. 211° C. |
| A297 | H | H | H | H | 2-CH=CHCH=CH-3 | 4-CN | 4-CF₃ | O | m.p. 200° C. |
| A298 | H | H | H | H | 2-CH=CHCH=CH-3 | 4-CN | 4-OCF₃ | O | m.p. 199° C. |
| A299 | H | H | H | H | 2-CH=CHCH=CH-3 | 4-CN | 4-OCF₂CHF₂ | O | m.p. 195° C. |
| A300 | CH₃ | H | H | H | H | H | H | O | m.p. 113° C. |
| A301 | CH₃ | H | H | H | H | H | 4-Cl | O | m.p. 132° C. |
| A302 | CH₃ | H | H | H | H | H | 4-OCF₃ | O | m.p. 108° C. |
| A303 | H | CH₃ | H | H | H | H | H | O | m.p. 111° C. |
| A304 | H | CH₃ | H | H | H | H | 2-Cl | O | m.p. 117° C. |
| A305 | H | CH₃ | H | H | H | H | 3-Cl | O | m.p. 108° C. |
| A306 | H | CH₃ | H | H | H | H | 4-Cl | O | m.p. 98° C. |
| A307 | H | CH₃ | H | H | H | H | 3,4-Cl₂ | O | Paste |
| A308 | H | CH₃ | H | H | H | H | 4-Br | O | m.p. 85° C. |
| A309 | H | CH₃ | H | H | H | H | 4-CH₃ | O | Paste |
| A310 | H | CH₃ | H | H | H | H | 4-CF₃ | O | m.p. 148° C. |
| A311 | H | CH₃ | H | H | H | H | 4-OCH₃ | O | Paste |
| A312 | H | CH₃ | H | H | H | H | 4-OCF₃ | O | m.p. 115° C. EZ-form |
| A313 | H | CH₃ | H | H | H | H | 4-OCF₃ | O | m.p. 95° C. E-form |
| A314 | H | CH₃ | H | H | H | H | 4-OCF₃ | O | m.p. 66° C. Z-form |
| A315 | H | CH₃ | H | H | H | 4-Cl | 4-Cl | O | m.p. 121° C. |
| A316 | H | CH₃ | H | H | H | 4-Cl | 3,4-Cl₂ | O | Paste |
| A317 | H | CH₃ | H | H | H | 4-Cl | 3-CF₃ | O | Paste |
| A318 | H | CH₃ | H | H | H | 4-Cl | 4-OCF₃ | O | m.p. 105° C. |
| A319 | H | CH₃ | H | H | 3-Cl | 4-CN | 4-Cl | O | m.p. 140° C. |
| A320 | H | CH₃ | H | H | 3-Cl | 4-CN | 4-CF₃ | O | m.p. 127° C. |
| A321 | H | CH₃ | H | H | 3-Cl | 4-CN | 4-OCF₃ | O | m.p. 98° C. |
| A322 | H | CH₃ | H | H | 4-Cl | H | 2-Cl | O | Paste |
| A323 | H | CH₃ | H | H | 4-Cl | H | 3-Cl | O | Paste |
| A324 | H | CH₃ | H | H | 4-Cl | H | 4-Cl | O | m.p. 109° C. |
| A325 | H | CH₃ | H | H | 4-Cl | H | 4-CF₃ | O | m.p. 119° C. |
| A326 | H | CH₃ | H | H | 4-Cl | H | 4-OCF₃ | O | Paste |
| A327 | H | CH₃ | H | H | 4-F | H | 4-OCF₃ | O | Paste |
| A328 | H | CH₃ | H | H | 4-CH₃ | H | 4-Cl | O | Paste |
| A329 | H | CH₃ | H | H | 4-CH₃ | H | 4-OCF₃ | O | Paste |
| A330 | H | H | OH | H | H | H | H | O | m.p. 167° C. |
| A331 | H | H | OH | H | H | H | 4-Cl | O | m.p. 188° C. |
| A332 | H | H | OH | H | H | H | 4-CF₃ | O | m.p. 176° C. |
| A333 | H | H | OH | H | H | H | 4-OCF₃ | O | m.p. 170° C. |
| A334 | H | H | OH | H | H | 4-Cl | 4-Cl | O | Paste |
| A335 | H | H | OH | H | H | 4-Cl | 4-OCF₃ | O | m.p. 185° C. E-form |
| A336 | H | H | OH | H | H | 4-Cl | 4-OCF₃ | O | m.p. 95° C. Z-form |
| A337 | H | H | OH | H | H | 4-CN | 4-Cl | O | Paste |
| A338 | H | H | OH | H | H | 4-CN | 4-OCF₃ | O | m.p. 113° C. |

TABLE 3-continued

| No. | R¹ | R² | R³ | R⁴ | X | Y | Z | W | Physical properties |
|---|---|---|---|---|---|---|---|---|---|
| A339 | H | H | OH | H | 2-Cl | 2-Cl | 4-Cl | O | Paste |
| A340 | H | H | OH | H | 2-Cl | 2-Cl | 4-OCF₃ | O | m.p. 76° C. |
| A341 | H | H | OH | H | 3-Cl | 3-Cl | H | O | m.p. 142° C. |
| A342 | H | H | OH | H | 3-Cl | 3-Cl | 4-Cl | O | m.p. 149° C. |
| A343 | H | H | OH | H | 3-Cl | 3-Cl | 4-CF₃ | O | m.p. 141° C. |
| A344 | H | H | OH | H | 3-Cl | 3-Cl | 4-OCF₃ | O | m.p. 146° C. |
| A345 | H | H | OH | H | 4-Cl | 4-Cl | 3-Cl | O | m.p. 81° C. |
| A346 | H | H | OH | H | 4-Cl | 4-Cl | 4-Cl | O | m.p. 59° C. |
| A347 | H | H | OH | H | 4-Cl | 4-Cl | 4-CF₃ | O | Paste |
| A348 | H | H | OH | H | 4-Cl | 4-Cl | 4-OCF₃ | O | Paste |
| A349 | H | H | OH | H | 2,4-Cl₂ | 2,4-Cl₂ | 4-OCF₃ | O | m.p. 72° C. |
| A350 | H | H | OH | H | 2,4-Cl₂ | 2,4-Cl₂ | 3,4-Cl₂ | O | m.p. 100° C. |
| A351 | H | H | OH | H | 4-F | 4-F | 4-Cl | O | m.p. 88° C. |
| A352 | H | H | OH | H | 4-F | 4-F | 4-OCF₃ | O | m.p. 168° C. |
| A353 | H | H | OH | H | 4-CH₃ | 4-CH₃ | 4-Cl | O | m.p. 180° C. |
| A354 | H | H | OH | H | 4-CH₃ | 4-CH₃ | 4-CF₃ | O | m.p. 184° C. |
| A355 | H | H | OH | H | 4-CH₃ | 4-CH₃ | 4-OCF₃ | O | m.p. 182° C. |
| A356 | H | H | OH | H | 4-OCH₃ | 4-OCH₃ | 4-Cl | O | m.p. 139° C. |
| A357 | H | H | OH | H | 4-OCH₃ | 4-OCH₃ | 4-CF₃ | S | m.p. 142° C. |
| A358 | H | H | OH | H | 4-CH₃ | 4-OCH₃ | 4-OCF₃ | O | m.p. 178° C. |
| A359 | H | H | OH | H | 4-N(CH₃)₂ | H | 4-OCF₃ | O | m.p. 167° C. |
| A360 | H | H | CH₃ | H | H | H | 4-Cl | O | m.p. 164° C. |
| A361 | H | H | CH₃ | H | H | H | 4-CF₃ | O | m.p. 150° C. |
| A362 | H | H | CH₃ | H | H | H | 4-OCF₃ | S | m.p. 132° C. |
| A363 | H | H | CH₃ | H | H | H | 3-Cl | O | m.p. 118° C. |
| A364 | H | H | OCH₃ | H | H | H | 4-Cl | O | m.p. 197° C. |
| A365 | H | H | OCH₃ | H | H | H | 3-Cl | O | m.p. 183° C. |
| A366 | H | H | OCH₃ | H | H | H | 3-CF₃ | O | m.p. 192° C. |
| A367 | H | H | OCH₃ | H | H | H | 4-CF₃ | O | m.p. 185° C. |
| A368 | H | H | OC₃H₇-i | H | H | H | 4-OCF₃ | O | m.p. 181° C. |
| A369 | H | H | OC₃H₇-i | H | H | H | 4-Cl | O | m.p. 155° C. |
| A370 | H | H | OC₃H₇-i | H | H | H | 4-OCF₃ | O | m.p. 209° C. |
| A371 | H | H | OC₄H₉-i | H | H | H | 4-Cl | O | m.p. 193° C. |
| A372 | H | H | OC₄H₉-i | H | H | H | 4-Cl | O | m.p. 176° C. |
| A373 | H | H | OCOCH₃ | H | H | H | 4-OCF₃ | O | m.p. 184° C. |
| A374 | H | H | OCOCH₃ | H | H | H | 4-OCF₃ | O | m.p. 182° C. |
| A375 | H | H | O—CO—⌬ | H | H | H | 4-OCF₃ | O | m.p. 168° C. |
| A376 | H | H | OH | CH₃ | H | H | 4-Cl | O | m.p. 115° C. |
| A377 | H | H | OH | CH₃ | H | H | 4-OCF₃ | O | m.p. 130° C. |
| A378 | H | H | =O | H | H | H | 4-CF₃ | O | m.p. 150° C. |
| A379 | H | H | =O | H | H | H | 4-OCF₃ | O | m.p. 132° C. |
| A380 | H | H | H | H | H | 2,4-F₂ | 4-Cl | O | m.p. 199° C. |
| A381 | H | H | H | H | H | 2,4-F₂ | 4-OCF₃ | O | m.p. 173° C. |
| A382 | H | H | H | H | H | 3,4-F₂ | 4-Cl | O | m.p. 203° C. |

TABLE 3-continued

| No. | R¹ | R² | R³ | R⁴ | X | Y | Z | W | Physical properties |
|---|---|---|---|---|---|---|---|---|---|
| A383 | H | H | H | H | H | 3,4-F₂ | 4-OCF₃ | O | m.p. 189° C. |
| A384 | H | H | H | H | H | 3,4-F₂ | 4-SCF₃ | O | m.p. 207° C. |
| A385 | H | H | H | H | H | 3,4-F₂ | 4-SOCF₃ | O | m.p. 188° C. |
| A386 | H | H | H | H | H | 3,4-F₂ | 4-SO₂CF₃ | O | m.p. 194° C. |
| A387 | H | H | H | H | H | 3,5-F₂ | 4-Cl | O | m.p. 205° C. |
| A388 | H | H | H | H | H | 3,5-F₂ | 4-Br | O | m.p. 201° C. |
| A389 | H | H | H | H | H | 3,5-F₂ | 4-OC₄H₉-i | O | m.p. 196° C. |
| A390 | H | H | H | H | H | 4-Cl | 4-Cl | O | m.p. 186° C. |
| A391 | H | H | H | H | H | 3,4-Cl₂ | 4-CF₃ | O | m.p. 208° C. |
| A392 | H | H | H | H | H | 3,4-Cl₂ | 4-OCF₃ | O | m.p. 215° C. |
| A393 | H | H | H | H | H | 3,4-Cl₂ | 4-OCF₂CHF₂ | O | m.p. 186° C. |
| A394 | H | H | H | H | H | 3,4-Cl₂ | 4-OCF₃ | O | m.p. 187° C. |
| A395 | H | H | H | H | H | 4-CF₃ | 4-OCF₃ | O | m.p. 196° C. |
| A396 | H | H | H | H | H | 4-⟨phenyl⟩ | 4-OCF₃ | O | m.p. 170° C. |
| A397 | H | H | H | H | H | 4-NHCHO | 4-OCF₃ | O | m.p. 193° C. |
| A398 | H | H | H | H | H | 4-NHCONHC₂H₅ | 4-OCF₃ | O | m.p. 209° C. |
| A399 | H | H | H | H | H | 4-NO₂ | 4-SOCF₃ | O | Glass-like amorphous substance |
| A400 | H | H | H | H | H | 4-OCF₃ | 4-OCF₃ | O | m.p. 168° C. |
| A401 | H | H | H | H | H | 4-OCF₃ | 4-OCF₃ | O | m.p. 204° C. |
| A402 | H | H | H | H | H | 4-OCH₂CF₃ | 4-OCF₃ | O | m.p. 169° C. |
| A403 | H | H | H | H | H | 4-SCHF₃ | 4-OCF₃ | O | m.p. 166° C. |
| A404 | H | H | H | H | H | 4-SOCHF₃ | 4-OCF₃ | O | m.p. 177° C. |
| A405 | H | H | H | H | 3-F | 4-CN | 4-SCF₃ | O | m.p. 214° C. |
| A406 | H | H | H | H | 3-F | 4-CN | 4-SOCF₃ | O | m.p. 228° C. |
| A407 | H | H | H | H | 3-F | 4-SO₂N(CH₃)₂ | 4-Cl | O | m.p. 234° C. |
| A408 | H | H | H | H | 3-F | 4-SO₂N(CH₃)₂ | 4-OCF₃ | O | m.p. 194° C. |
| A409 | H | H | H | H | 3-F | 4-CN | 4-OCF₂Br | O | m.p. 186° C. |
| A410 | H | H | H | H | 4-F | 4-CN | 4-SCF₃ | O | m.p. 221° C. |
| A411 | H | H | H | H | 4-F | 4-CN | 4-SOCF₃ | O | m.p. 224° C. |
| A412 | H | H | H | H | 3-Cl | 4-CN | 4-SO₂CF₃ | O | m.p. 165° C. |
| A413 | H | H | H | H | 3-Cl | 4-CN | 2,3,4-Cl₃ | O | m.p. 237° C. |
| A414 | H | H | H | H | 3-Cl | 4-CN | 2,3,4,5-Cl₄ | O | m.p. 255° C. |
| A415 | H | H | H | H | 3-Cl | 4-CN | 4-I | O | m.p. 207° C. |
| A416 | H | H | H | H | 3-Cl | 4-CN | 4-C₆H₁₃-n | O | m.p. 173° C. |
| A417 | H | H | H | H | 3-Cl | 4-CN | 4-COCH₃ | O | m.p. 218° C. |
| A418 | H | H | H | H | 3-Cl | 4-CN | 3-Cl-4-OCF₂CHF₃ | O | m.p. 211° C. |
| A419 | H | H | H | H | 3-Cl | 4-CN | 4-O—COCH₃ | O | m.p. 177° C. |
| A420 | H | H | H | H | 3-Cl | 4-CN | 4-OSO₂CF₃ | O | m.p. 199° C. |
| A421 | H | H | H | H | 3-Cl | 4-CN | 4-SOCF₃ | O | m.p. 157° C. Z-form |
| A422 | H | H | H | H | 3-Cl | 2-Cl-4-CN | 4-CF₃ | O | m.p. 199° C. |
| A423 | H | H | H | H | 3-Cl | 2-Cl-4-CN | 4-OCF₃ | O | m.p. 188° C. |

TABLE 3-continued

| No. | R¹ | R² | R³ | R⁴ | X | Y | Z | W | Physical properties |
|---|---|---|---|---|---|---|---|---|---|
| A424 | H | H | H | H | 3-Cl | 2-Cl-4-CN | 4-SCF$_3$ | O | m.p. 197° C. |
| A425 | H | H | H | H | 3-Cl | 3-Cl-4-CN | 4-OCF$_3$ | O | m.p. 180° C. |
| A426 | H | H | H | H | 3-Cl | 2-CH$_3$-4-CN | 4-Cl | O | m.p. 209° C. |
| A427 | H | H | H | H | 3-Cl | 2-CH$_3$-4-CN | 4-OCF$_3$ | O | m.p. 164° C. |
| A428 | H | H | H | H | 3-Cl | 2-CH$_3$-4-CN | 4-SCF$_3$ | O | m.p. 189° C. |
| A429 | H | H | H | H | 3-Cl | 2-CH$_3$-4-CN | 4-SOCF$_3$ | O | m.p. 207° C. |
| A430 | H | H | H | H | 3-Cl | 2-CH$_3$-4-CN | 4-SO$_2$CF$_3$ | O | m.p. 205° C. |
| A431 | H | H | H | H | 3-Cl | 3-CH$_3$-4-CN | 4-Cl | O | m.p. 209° C. |
| A432 | H | H | H | H | 3-Cl | 3-CH$_3$-4-CN | 4-OCF$_3$ | O | m.p. 199° C. |
| A433 | H | H | H | H | 3-Cl | 3-CH$_3$-4-CN | 4-SCF$_3$ | O | m.p. 213° C. |
| A434 | H | H | H | H | 3-Cl | 3-CH$_3$-4-CN | 4-SOCF$_3$ | O | m.p. 180° C. |
| A435 | H | H | H | H | 3-Cl | 3-CH$_3$-4-CN | 4-SO$_2$CF$_3$ | O | m.p. 152° C. |
| A436 | H | H | H | H | 3-Cl | 3,4-(CN)$_2$ | 4-OCF$_3$ | O | m.p. 211° C. |
| A437 | H | H | H | H | 3-Cl | 4-COOCH$_3$ | 4-OCF$_3$ | O | m.p. 160° C. |
| A438 | H | H | H | H | 3-Cl | 4-OH | 4-OCF$_3$ | O | m.p. 193° C. |
| A439 | H | H | H | H | 3-Cl | 4-OCHF$_2$ | 4-CF$_3$ | O | m.p. 181° C. |
| A440 | H | H | H | H | 3-Cl | 4-OCHF$_2$ | 4-OCF$_3$ | O | m.p. 170° C. |
| A441 | H | H | H | H | 3-Cl | 4-OCHF$_2$ | 4-SCF$_3$ | O | m.p. 193° C. |
| A442 | H | H | H | H | 3-Cl | 4-OSO$_2$CH$_3$ | 4-OCF$_3$ | O | m.p. 195° C. |
| A443 | H | H | H | H | 3-Cl | 4-OSO$_2$CF$_3$ | 4-OCF$_3$ | O | m.p. 173° C. |
| A444 | H | H | H | H | 3-Cl | 4-CN | 2,3,4-Cl$_3$ | O | m.p. 247° C. |
| A445 | H | H | H | H | 3-Br | 4-CN | 2,3,4,5-Cl$_4$ | O | m.p. 250° C. |
| A446 | H | H | H | H | 3-Br | 4-CN | 4-C$_6$H$_{13}$-n | O | m.p. 169° C. |
| A447 | H | H | H | H | 3-Br | 4-CN | 3-Cl-4-OCF$_2$CHF$_2$ | O | m.p. 228° C. |
| A448 | H | H | H | H | 3-CHF$_2$ | 4-CN | 4-OCF$_3$ | O | m.p. 177° C. |
| A449 | H | H | H | H | 3-CF$_3$ | 4-CN | 4-OCF$_2$Br | O | m.p. 172° C. |
| A450 | H | H | H | H | 3-CF$_3$ | 4-CN | 4-SCF$_3$ | O | m.p. 215° C. |
| A451 | H | H | H | H | 3-CF$_3$ | 4-CN | 4-SOCF$_3$ | O | m.p. 210° C. |
| A452 | H | H | H | H | 3-CF$_3$ | 4-CN | 4-SO$_2$CF$_3$ | O | m.p. 225° C. |
| A453 | H | H | H | H | 3-CF$_3$ | 4-CN | 4-OCF$_3$ | O | m.p. 211° C. |
| A454 | H | H | H | H | 3-F-5-CF$_3$ | 4-CN | 4-CF$_3$ | O | m.p. 196° C. |
| A455 | H | H | H | H | 3-CH$_2$OCH$_3$ | 4-CN | 4-OCF$_3$ | O | m.p. 197° C. |
| A456 | H | H | H | H | 3-CH$_2$OCH$_3$ | 4-CN | 4-OCF$_3$ | O | m.p. 190° C. |
| A457 | H | H | H | H | 3-CH[OCH$_2$CH$_2$O] | 4-CN | 4-OCF$_3$ | O | m.p. 169° C. |
| A458 | H | H | H | H | 3-OH | 4-CN | 4-OCF$_3$ | O | m.p. 224° C. |
| A459 | H | H | H | H | 3-OCH$_2$CH=CH$_2$ | 4-CN | 4-OCF$_3$ | O | m.p. 160° C. |
| A460 | H | H | H | H | 3-OCHF$_2$ | 4-CN | 4-CF$_3$ | O | m.p. 188° C. |
| A461 | H | H | H | H | 3-OCHF$_2$ | 4-CN | 4-SCF$_3$ | O | m.p. 204° C. |
| A462 | H | H | H | H | 3-OCHF$_2$ | 4-CN | 4-SOCF$_3$ | O | m.p. 195° C. |
| A463 | H | H | H | H | 3-OCHF$_2$ | 4-CN | 4-SO$_2$CF$_3$ | O | m.p. 206° C. |
| A464 | H | H | H | H | 3-OCF$_3$ | 4-CN | 4-CF$_3$ | O | m.p. 159° C. |
| A465 | H | H | H | H | 3-OCF$_3$ | 4-CN | 4-OCF$_3$ | O | m.p. 171° C. |
| A466 | H | H | H | H | 3-OCF$_3$ | 4-CN | 4-SCF$_3$ | O | m.p. 202° C. |

TABLE 3-continued

| No. | R¹ | R² | R³ | R⁴ | X | Y | Z | W | Physical properties |
|---|---|---|---|---|---|---|---|---|---|
| A467 | H | H | H | H | 3-OCF$_3$ | 4-CN | 4-SOCF$_3$ | O | m.p. 200° C. |
| A468 | H | H | H | H | 3-OCH$_2$COCH$_3$ | 4-CN | 4-OCF$_3$ | O | m.p. 198° C. |
| A469 | H | H | H | H | 3-OCH$_2$CO$_2$C$_2$H$_5$ | 4-CN | 4-OCF$_3$ | O | m.p. 172° C. |
| A470 | H | H | H | H | 3-O—COC$_3$H$_5$-c | 4-CN | 4-OCF$_3$ | O | m.p. 200° C. |
| A471 | H | H | H | H | 3-O—CON(CH$_3$)$_2$ | 4-CN | 4-OCF$_3$ | O | m.p. 197° C. |
| A472 | H | H | H | H | 3-O—CO$_2$CH$_3$ | 4-CN | 4-OCF$_3$ | O | m.p. 180° C. |
| A473 | H | H | H | H | 3-OSO$_2$CH$_3$ | 4-CN | 4-OCF$_3$ | O | m.p. 201° C. |
| A474 | H | H | H | H | 3-CF$_3$ | 4-CN | 4-SC$_3$F$_7$-n | | |
| A475 | H | H | H | H | 3-CF$_3$ | 4-CN | 4-(cyclopropyl-CCl$_2$) | O | m.p. 248° C. |
| A476 | H | H | H | H | 3-CF$_3$ | 4-CN | 4-SOC$_3$F$_7$-n | O | m.p. 207° C. |
| A477 | H | H | H | H | 3-CF$_3$ | 4-CN | 4-SO$_2$C$_3$F$_7$-n | O | m.p. 231° C. |
| A478 | H | H | H | H | 3-CF$_3$ | 4-CN | 4-OCF$_3$ | O | m.p. 152° C. Z-form |
| A479 | H | H | H | H | 3-CF$_3$ | 4-CN | 4-Cl | O | m.p. 165° C. |
| A480 | H | H | H | H | 3-CF$_3$ | 4-CH$_3$ | 4-OCF$_3$ | O | m.p. 184° C. |
| A481 | H | H | H | H | 4-F | 4-NO$_2$ | 4-Cl | S | m.p. 178° C. |
| A482 | H | H | H | H | 3-F | 4-CN | 4-CH$_3$ | S | m.p. 148° C. |
| A483 | H | H | H | H | H | 3-CH=CH—CH=N-4 | 4-OCF$_3$ | O | m.p. 214° C. |
| A484 | H | H | H | H | H | 3-CH=CH—CH=N-4 | 4-OCF$_3$ | O | m.p. >214° C. Hydrochloride |
| A485 | H | H | H | H | H | 3-CH=CH—CH=N-4 | 4-ClF | O | m.p. 210° C. |
| A486 | H | H | H | H | 3-CF$_3$ | 4-CN | 4-(cyclopropyl-CCl$_2$) | | m.p. 221° C. |

In the table, -c denotes an alicyclic compound and m.p. denotes melting point.

Table 4 shows $^1$-NMR data of the compounds having physical properties as paste listed in Table 3.

TABLE 4

| No. | $^1$H-NMR(CDCl$_3$/TMS, δ value, ppm.) |
|---|---|
| A055 | 3.88+4.23(s, 2H), 6.52+6.54(t, 1H), 6.95+7.77(m, 13H), 8.73+8.98+9.20+9.39(s, 2H). (Mixture of E- and Z-forms) |
| A307 | 2.70(s, 3H), 3,87(s, 2H), 6.90–7.60(m, 13H), 8.23(bs, 1H). |
| A309 | 2.23(s, 3H), 3.17(s, 3H), 4.20(s, 2H), 6.50–7.83(m, 15H). |
| A311 | 2.73+3.20(s, 3H), 3.70(s, 3H), 3.90+4.23(s, 2H), 6.60–8.00(m, 14H), 8.17(bs, 1H). (Mixture of E- and Z-forms) |
| A316 | 2.60+3.20(s, 3H), 3.87+4.20(s, 2H), 6.27–8.27(m, 13H). (Mixture of E- and Z-forms) |
| A317 | 2.73+3.23(s, 3H), 3.90+4.23(s, 2H), 6.73–8.13(m, 13H), 8.40(bs, 1H). (Mixture of E- and Z-forms) |
| A322 | 3.23(s, 3H), 4.20(s, 2H), 6.67–8.43(m, 13H), 8.77(bs, 1H). |
| A323 | 2.73+3.23(s, 3H), 3.87+4.20(s, 2H), 6.80–8.00(m, 14H). (Mixture of E- and Z-forms) |
| A326 | 2.73+3.20(s, 3H), 3.87+4.20(s, 2H), 6.43–7.93(m, 13H), 8.00(bs, 1H). (Mixture of E- and Z-forms) |
| A327 | 2.73(s, 3H), 3.87(s, 1H), 6.73–7.90(m, 13H), 8.30(bs, 1H). |
| A328 | 2.23+2.33(s, 3H), 2.70+3.17(s, 3H), 3.87+4.17(s, 2H), 6.43–7.90(m, 13H). |

TABLE 4-continued

| No. | $^1$H-NMR(CDCl$_3$/TMS, δ value, ppm.) |
|---|---|
| A329 | (Mixture of E- and Z-forms) 2.30(s, 2H), 3.17(s,3H), 4.17(s, 2H), 6.83–8.30(m, 14H). |
| A334 | 6.29(s, 1H), 7.65–7.92(m, 13H), 9.14(bs, 1H), 10.70(bs, 1H), (DMSO-d$_6$) |
| A337 | 3.88(bs, 1H), 3.87(s, 2H), 6.91–7.55(m, 13H), 7.73(s, 1H), 8.13(bs, 1H). |
| A339 | 3.72(bs, 1H), 6.08(s, 1H), 6.77–7.68(m, 12H), 8.17(bs, 1H), 10.58(bs, 1H). |
| A347 | 3.75(bs, 1H), 5.60(d, 1H), 6.94–7.61(m, 12H), 8.18(s, 1H), 10.80(s, 1H). |
| A348 | 3.75(bs, 1H), 5.31(d, 1H), 6.92–7.65(m, 12H), 8.13(s, 1H), 10.75(s, 1H). |
| A399 | 4.31(s, 2H), 7.31–8.14(m, 13H), 8.63(s, 1H), 9.15(s, 1H). |

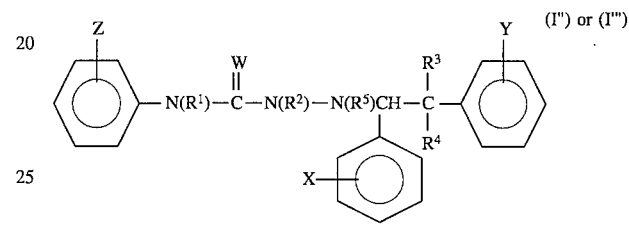

(I″) or (I‴)

TABLE 5

(Wherein each of R$^1$ and R$^4$ is a hydrogen atom.)

| No. | R$^2$ | R$^3$ | R$^5$ | X | Y | Z | W | Physical properties |
|---|---|---|---|---|---|---|---|---|
| B001 | H | H | H | H | H | 4-Cl | O | m.p. 211° C. |
| B002 | H | H | H | H | H | 4-OCF$_3$ | O | m.p. 194° C. |
| B003 | H | H | H | H | 4-Cl | 4-OCF$_3$ | O | m.p. 209° C. |
| B004 | H | H | H | H | 4-Cl | 4-OCF$_2$CHF$_2$ | O | m.p. 202° C. |
| B005 | H | H | H | H | 4-Cl | 4-O—⌬—CF$_3$ | 0 | m.p. 215° C. |
| B006 | H | H | H | H | 4-CN | 4-OCF$_3$ | O | m.p. 204° C. |
| B007 | H | H | H | H | 4-NHCOCH$_3$ | 4-OCF$_3$ | O | m.p. 206° C. |
| B008 | H | H | H | H | 4-NO$_2$ | 4-OCF$_3$ | O | m.p. 188° C. |
| B009 | H | H | H | H | 4-OCHF$_2$ | 4-OCF$_3$ | O | m.p. 202° C. |
| B010 | H | H | H | 3-F | 4-Cl | 4-OCF$_3$ | O | m.p. 203° C. |
| B011 | H | H | H | 4-F | 4-Cl | 4-OCF$_3$ | O | m.p. 207° C. |
| B012 | H | H | H | 3-Cl | 4-Cl | 4-CF$_3$ | O | m.p. 189° C. |
| B013 | H | H | H | 3-Cl | 4-Cl | 4-OCF$_3$ | O | m.p. 176° C. |
| B014 | H | H | H | 3-Cl | 4-CN | 4-CF$_3$ | O | m.p. 198° C. |
| B015 | H | H | H | 3-Cl | 4-CN | 4-OCF$_3$ | O | m.p. 193° C. |
| B016 | H | H | H | 3-Cl | 4-CN | 4-OCF$_2$CHF$_3$ | O | m.p. 164° C. |

TABLE 5-continued (Wherein each of $R^1$ and $R^4$ is a hydrogen atom.)

| No. | $R^2$ | $R^3$ | $R^5$ | X | Y | Z | W | Physical properties |
|---|---|---|---|---|---|---|---|---|
| B017 | H | H | H | 3-Cl | 4-CN | 4-OC$_4$H$_9$-t | O | m.p. 186° C. |
| B018 | H | H | H | 3-Cl | 4-CN | 4-SCF$_3$ | O | m.p. 177° C. |
| B019 | H | H | H | 3-Cl | 4-CN | 4-SOCF$_3$ | O | m.p. 178° C. |
| B020 | H | H | H | 3-Cl | 4-CN | 4-SO$_2$CF$_3$ | O | m.p. 170° C. |
| B021 | H | H | H | 4-Cl | 4-Cl | 4-CF$_3$ | O | m.p. 195° C. |
| B022 | H | H | H | 4-Cl | 4-Cl | 4-OCF$_3$ | O | m.p. 165° C. |
| B023 | H | H | H | 4-Cl | 4-CN | 4-OCF$_3$ | O | m.p. 210° C. |
| B024 | H | H | H | 3-Br | 4-CN | 4-OCF$_3$ | O | m.p. 187° C. |
| B025 | H | H | H | 3-CF$_3$ | 4-CN | 4-OCF$_3$ | O | m.p. 165° C. |
| B026 | H | H | H | 3-CF$_3$ | 4-CN | 4-SCF$_3$ | O | m.p. 164° C. |
| B027 | H | H | H | 4-OCHF$_2$ | H | 4-Cl | O | m.p. 192° C. |
| B028 | H | H | H | 4-OCHF$_2$ | H | 4-OCF$_3$ | O | m.p. 217° C. |
| B029 | H | H | H | 4-OCHF$_2$ | H | 4-SCF$_3$ | O | m.p. 209° C. |
| B030 | H | H | H | 3-O-C$_6$H$_5$ | 4-CN | 4-OCF$_3$ | O | m.p. 164° C. |
| B031 | H | H | H | H | 4-Cl | 4-OCF$_3$ | S | m.p. 171° C. |
| B032 | H | H | H | 3-Cl | 4-CN | 4-OCF$_3$ | S | m.p. 149° C. |
| B033 | H | H | H | 4-Cl | 4-CN | 4-OCF$_3$ | S | m.p. 195° C. |
| B034 | H | H | H | 3-CF$_3$ | 4-CN | 4-OCF$_3$ | S | m.p. 209° C. |
| B035 | H | H | COCH$_3$ | 3-Cl | 4-CN | 4-OCF$_3$ | O | m.p. 178° C. |
| B036 | H | H | CO-C$_6$H$_5$ | 3-Cl | 4-CN | 4-OCF$_3$ | O | m.p. 221° C. |
| B037 | H | H | CONHC$_2$H$_5$ | 3-Cl | 4-CN | 4-OCF$_3$ | O | m.p. 201° C. |
| B038 | H | OH | H | H | H | 4-CF$_3$ | O | m.p. 200° C. |
| B039 | H | OH | H | H | H | 4-OCF$_3$ | O | m.p. 190° C. |
| B040 | H | OCH$_3$ | H | H | H | 4-Cl | O | m.p. 195° C. |
| B041 | H | OCH$_3$ | H | H | H | 4-OCF$_3$ | O | m.p. 183° C. |
| B042 | H | OCH$_3$ | H | H | H | 4-OCF$_3$ | O | m.p. 186° C. |
| B043 | CH$_3$ | H | H | 3-Cl | 4-CN | 4-OCF$_3$ | O | m.p. 156° C. |
| B044 | H | H | H | H | 4-F | 4-CF$_3$ | O | m.p. 211° C. |
| B045 | H | H | H | H | 4-F | 4-OCF$_3$ | O | m.p. 209° C. |
| B046 | H | H | H | H | 2,4-F$_2$ | 4-Cl | O | m.p. 229° C. |
| B047 | H | H | H | H | 2,4-F$_2$ | 4-OCF$_3$ | O | m.p. 212° C. |
| B048 | H | H | H | H | 3,4-F$_2$ | Cl | O | m.p. |

TABLE 5-continued (Wherein each of R¹ and R⁴ is a hydrogen atom.)

| No. | R² | R³ | R⁵ | X | Y | Z | W | Physical properties |
|---|---|---|---|---|---|---|---|---|
| B049 | H | H | H | H | 3,4-F₂ | 4-OCF₃ | O | m.p. 201° C. |
| B050 | H | H | H | H | 3,4-F₂ | 4-SCF₃ | O | m.p. 170° C. |
| B051 | H | H | H | H | 3,4-F₂ | 4-SOCF₃ | O | m.p. 163° C. |
| B052 | H | H | H | H | 3,4-F₂ | 4-SO₂CF₃ | O | m.p. 163° C. |
| B053 | H | H | H | H | 3,5-F₂ | 4-Cl | O | m.p. 182° C. |
| B054 | H | H | H | H | 3,5-F₂ | 4-Br | O | m.p. 185° C. |
| B055 | H | H | H | H | 4-Br | 4-Cl | O | m.p. 194° C. |
| B056 | H | H | H | H | 4-Br | 4-CF₃ | O | m.p. 233° C. |
| B057 | H | H | H | H | 4-Br | 4-OCF₃ | O | m.p. 227° C. |
| B058 | H | H | H | H | 4-CH₃ | 4-CF₃ | O | m.p. 201° C. |
| B059 | H | H | H | H | 4-CH₃ | 4-OCF₃ | O | m.p. 218° C. |
| B060 | H | H | H | H | 4-CF₃ | 4-OCF₃ | O | m.p. 201° C. |
| B061 | H | H | H | H | 3-CN | 4-CF₃ | O | m.p. 215° C. |
| B062 | H | H | H | H | 3-CN | 4-OCF₃ | O | m.p. 186° C. |
| B063 | H | H | H | H | 3-CN | 4-OCF₂CHF₂ | O | m.p. 176° C. |
| B064 | H | H | H | H | 4-NH₂ | 4-OCF₃ | O | m.p. 153° C. |
| B065 | H | H | H | H | 2-NO₂ | 4-OCF₃ | O | m.p. 188° C. |
| B066 | H | H | H | H | 4-NO₂ | 4-SCF₃ | O | m.p. 197° C. |
| B067 | H | H | H | H | 4-OCF₃ | 4-OCF₃ | O | m.p. 188° C. |
| B068 | H | H | H | H | 4-OCF₃ | 4-SCF₃ | O | m.p. 206° C. |
| B069 | H | H | H | H | 4-SCHF₂ | 4-OCF₃ | O | m.p. 181° C. |
| B070 | H | H | H | 3-F | 4-CN | 4-OCF₃ | O | m.p. 195° C. |
| B071 | H | H | COCH₃ | 3-F | 4-CN | 4-OCF₃ | O | m.p. 189° C. |
| B072 | H | H | COC₄H₉-t | 3-F | 4-CN | 4-OCF₃ | O | m.p. 193° C. |
| B073 | H | H | H | 3-F | 4-CN | 4-OCF₂Br | O | m.p. 218° C. |
| B074 | H | H | H | 3-F | 4-CN | 4-SCF₃ | O | m.p. 201° C. |
| B075 | H | H | H | 3-F | 4-CN | 4-SOCF₃ | O | m.p. 189° C. |
| B076 | H | H | H | 3-F | 4-SO₂N(CH₃)₂ | 4-Cl | O | m.p. 166° C. |
| B077 | H | H | H | 3-F | 4-SO₂N(CH₃)₂ | 4-OCF₃ | O | m.p. 216° C. |
| B078 | H | H | H | 4-F | 4-F | 4-OCF₃ | O | m.p. 214° C. |
| B079 | H | H | H | 4-F | 4-CN | 4-OCF₃ | O | m.p. 174° C. |
| B080 | H | H | H | 4-F | 4-CN | 4-SCF₃ | O | m.p. 194° C. |
| B081 | H | H | H | 4-F | 4-CN | 4-SOCF₃ | O | m.p. 211° C. |
| B082 | H | H | H | 4-F | 4-CN | 4-SO₂CF₃ | O | m.p. 198° C. 177° C. |

TABLE 5-continued (Wherein each of R¹ and R⁴ is a hydrogen atom.)

| No. | R² | R³ | R⁵ | X | Y | Z | W | Physical properties |
|---|---|---|---|---|---|---|---|---|
| B083 | H | H | H | 3-Cl | 4—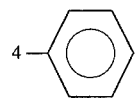 | 4-OCF₃ | O | m.p. 207° C. |
| B084 | H | H | H | 3-Cl | 4-CN | 4-I | O | m.p. 218° C. |
| B085 | H | H | COC₂H₅ | 3-Cl | 4-CN | 4-OCF₃ | O | m.p. 202° C. |
| B086 | H | H | COC₃H₇-n | 3-Cl | 4-CN | 4-OCF₃ | O | m.p. 142° C. |
| B087 | H | H | COC₃H₅c | 3-Cl | 4-CN | 4-OCF₃ | O | m.p. 242° C. |
| B088 | H | H | COC₄H₉-t | 3-Cl | 4-CN | 4-OCF₃ | O | m.p. 132° C. |
| B089 | H | H | COC₉H₁₉-n | 3-Cl | 4-CN | 4-OCF₃ | O | m.p. 163° C. |
| B090 | H | H | COCH₂Cl | 3-Cl | 4-CN | 4-OCF₃ | O | m.p. 191° C. |
| B091 | H | H | 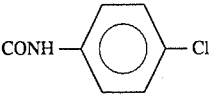 | 3-Cl | 4-CN | 4-OCF₃ | O | m.p. 210° C. |
| B092 | H | H | CO₂CH₃ | 3-Cl | 4-CN | 4-OCF₃ | O | m.p. 199° C. |
| B093 | H | H | H | 3-Cl | 4-CN | 4-OSO₂CF₃ | O | m.p. 207° C. |
| B094 | H | H | H | 3-Cl | 2-Cl-4-CN | 4-CF₃ | O | m.p. 203° C. |
| B095 | H | H | H | 3-Cl | 2-Cl-4-CN | 4-OCF₃ | O | m.p. 196° C. |
| B096 | H | H | H | 3-Cl | 2-Cl-4-CN | 4-SCF₃ | O | m.p. 205° C. |
| B097 | H | H | H | 3-Cl | 2-CH₃-4-CN | 4-Cl | O | m.p. 183° C. |
| B098 | H | H | H | 3-Cl | 2-CH₃-4-CN | 4-OCF₃ | O | m.p. 191° C. |
| B099 | H | H | H | 3-Cl | 2-CH₃-4-CN | 4-SCF₃ | O | m.p. 192° C. |
| B100 | H | H | H | 3-Cl | 2-CH₃-4-CN | 4-SOCF₃ | O | m.p. 180° C. |
| B101 | H | H | H | 3-Cl | 2-CH₃-4-CN | 4-SO₂CF₃ | O | m.p. 195° C. |
| B102 | H | H | H | 3-Cl | 3-CH₃-4-CN | 4-Cl | O | m.p. 210° C. |
| B103 | H | H | H | 3-Cl | 3-CH₃-4-CN | 4-OCF₃ | O | m.p. 189° C. |
| B104 | H | H | H | 3-Cl | 3-CH₃-4-CN | 4-SCF₃ | O | m.p. 179° C. |
| B105 | H | H | H | 3-Cl | 3-CH₃-4-CN | 4-SOCF₃ | O | m.p. 188° C. |
| B106 | H | H | H | 3-Cl | 3-CH₃-4-CN | 4-SO₂CF₃ | O | m.p. 191° C. |
| B107 | H | H | H | 3-Cl | 4-(CN)₂ | 4-OCF₃ | O | m.p. 208° C. |
| B108 | H | H | H | 3-Cl | 4-OCF₃ | 4-CF₃ | O | m.p. 184° C. |
| B109 | H | H | H | 3-Cl | 4-OCHF₂ | 4-OCF₃ | O | m.p. 172° C. |
| B110 | H | H | H | 3-Cl | 4-OCHF₂ | 4-SCF₃ | O | m.p. 158° C. |
| B111 | H | H | H | 3-Cl | 4-OSO₂CH₃ | 4-OCF₃ | O | m.p. 185° C. |
| B112 | H | H | H | 3-Cl | 4-OSO₂CF₃ | 4-OCF₃ | O | m.p. 193° C. |
| B113 | H | H | H | 3-Br | 4-CN | 4-C₆H₁₃-n | O | m.p. 183° C. |
| B114 | H | H | COCH₃ | 3-Br | 4-CN | 4-OCF₃ | O | m.p. 198° C. |

TABLE 5-continued (Wherein each of R¹ and R⁴ is a hydrogen atom.)

| No. | R² | R³ | R⁵ | X | Y | Z | W | Physical properties |
|---|---|---|---|---|---|---|---|---|
| B115 | H | H | COC₂H₅ | 3-Br | 4-CN | 4-OCF₃ | O | m.p. 200° C. |
| B116 | H | H | COC₄H₉-t | 3-Br | 4-CN | 4-OCF₃ | O | m.p. 230° C. |
| B117 | H | H | H | 3-CHF₂ | 4-CN | 4-OCF₃ | O | Glass-like amorphous substance |
| B118 | H | H | H | 3-CF₃ | 4-CN | 4-OCF₃ | O | m.p. 131° C. − isomer |
| B119 | H | H | H | 3-CF₃ | 4-CN | 4-OCF₃ | O | m.p. 126° C. + isomer |
| B120 | H | H | COCH₃ | 3-CF₃ | 4-CN | 4-OCF₃ | O | m.p. 191° C. |
| B121 | H | H | COC₃H₇-i | 3-CF₃ | 4-CN | 4-OCF₃ | O | m.p. 208° C. |
| B122 | H | H | COC₄H₉-t | 3-CF₃ | 4-CN | 4-OCF₃ | O | m.p. 183° C. |
| B123 | H | H | CONH-C₆H₄-OCF₃ | 3-CF₃ | 4-CN | 4-OCF₃ | O | m.p. 251° C. |
| B124 | H | H | H | 3-CF₃ | 4-CN | 4-OCF₂Br | O | m.p. 190° C. |
| B125 | H | H | H | 3-CF₃ | 4-CN | 4-SOCF₃ | O | Glass-like amorphous substance |
| B126 | H | H | H | 3-CF₃ | 4-CN | 4-SO₂CF₃ | O | Glass-like amorphous substance |
| B127 | H | H | H | 4-CF₃ | 4-CN | 4-OCF₃ | O | m.p. 189° C. |
| B128 | H | H | H | 3-CH₂OCH₃ | 4-CN | 4-CF₃ | O | m.p. 153° C. |
| B129 | H | H | H | 3-CH₂OCH₃ | 4-CN | 4-OCF₃ | O | m.p. 146° C. |
| B130 | H | H | H | 3-OCH₃ | 4-CN | 4-OCF₃ | O | m.p. 166° C. |
| B131 | H | H | H | 3-OC₃H₇-i | 4-CN | 4-OCF₃ | O | m.p. 147° C. |
| B132 | H | H | H | 3-OCHF₂ | 4-CN | 4-OCF₃ | O | m.p. 118° C. |
| B133 | H | H | H | 3-OCHF₂ | 4-CN | 4-SCF₃ | O | m.p. 118° C. |
| B134 | H | H | H | 3-OCHF₂ | 4-CN | 4-SOCF₃ | O | Glass-like amorphous substance |
| B135 | H | H | H | 3-OCF₃ | 4-CN | 4-CF₃ | O | m.p. 178° C. |
| B136 | H | H | H | 3-OCF₃ | 4-CN | 4-OCF₃ | O | m.p. 147° C. |
| B137 | H | H | H | 3-OCF₃ | 4-CN | 4-SCF₃ | O | m.p. 156° C. |
| B138 | H | H | H | 3-OCF₃ | 4-CN | 4-SOCF₃ | O | Glass-like |

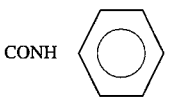

TABLE 5-continued (Wherein each of $R^1$ and $R^4$ is a hydrogen atom.)

| No. | $R^2$ | $R^3$ | $R^5$ | X | Y | Z | W | Physical properties |
|---|---|---|---|---|---|---|---|---|
| B139 | H | H | H | 3-OCH$_2$CO$_2$CH$_3$ | 4-CN | 4-OCF$_3$ | O | amorphous substance Glass-like amorphous substance |
| B140 | H | H | H | 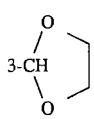 3-CH(O-O) | 4-CN | 4-OCF$_3$ | O | m.p. 154° C. |
| B141 | H | H | H | 3-OCO$_2$CH$_3$ | 4-CN | 4-OCF$_3$ | O | Glass-like amorphous substance |
| B142 | H | H | H | H | 3-CN | 4-OCF$_3$ | S | m.p. 120° C. |
| B143 | H | H | H | 4-F | 4-NO$_2$ | 4-Cl | S | m.p. 183° C. |
| B144 | H | H | H | 3-CF$_3$ | 4-CH$_3$ | 4-OCF$_3$ | O | m.p. 166° C. |
| B145 | H | H | COCO—OC$_2$H$_5$ | 3-Cl | 4-CN | 4-OCF$_3$ | O | m.p. 192° C. |
| B146 | H | H | H | H | 3-CH=CH—CH=N-4 | 4-OCF$_3$ | O | m.p. >300° C. Hydrochloride |

Compounds B041 and B042 are diastereomers, and the Rf value of compound B041 is higher than that of compound B042. M.p. in the "physical properties" column denotes melting point.

Table 6 shows $^1$-NMR data of the compounds having physical properties as glass like amorphous substance listed in Table 5.

TABLE 6

| No. | $^1$H-NMR(CDCl$_3$/TMS, δ value, ppm.) |
|---|---|
| B117 | 3.07(dd, 1H), 3.18(dd, 1H), 4.06–4.18(m, 2H), 6.02(s, 1H), 6.62(t, 1H), 7.06–7.61(m, 12H), 7.73(s, 1H). |
| B125 | 3.12(dd, 1H), 3.23(dd, 1H), 4.12–4.32(m, 2H), 6.13(bs, 1H), 7.24–7.93(m, 12H), 8.08(bs, 1H). |
| B126 | 3.11(dd, 1H), 3.23(dd, 1H), 4.13–4.28(m, 2H), 5.97(s, 1H), 7.25–7.75(m, 12H), 7.90–8.00(bs, 1H). |
| B134 | 3.05(dd, 1H), 3.18(dd, 1H), 4.05–4.15(m, 1H), 4.39(d, 1H), 6.46(t, 1H), 6.49(bs, 1H), 6.98–7.67(m, 12H), 8.04(s, 1H). |
| B138 | 3.04(dd, 1H), 3.16(dd, 1H), 4.03–4.21(m, 2H), 6.15(s, 1H), 6.95–7.65(m, 12H), 7.80(bs, 1H). |
| B139 | 3.07(dd, 1H), 3.14(dd, 1H), 3.81(s, 3H), 3.97–4.11(m, 2H), 4.62(s, 2H), 5.72(s, 1H), 6.79–7.63(m, 12H), 7.73(s, 1H). |
| B141 | 3.05(dd, 1H), 3.14(dd, 1H), 3.90(s, 3H), 3.96–4.16(m, 2H), 5.84(s, 1H), 6.69–7.61(m, 12H), 7.70(s, 1H). |

As the compound of the general formula (VIII), i.e., the starting compound for producing the hydrazinecarboxamide derivative of the general formula (I) of the present invention, there may be used either commercially available one or one which is produced, for example, by the production process illustrated below.

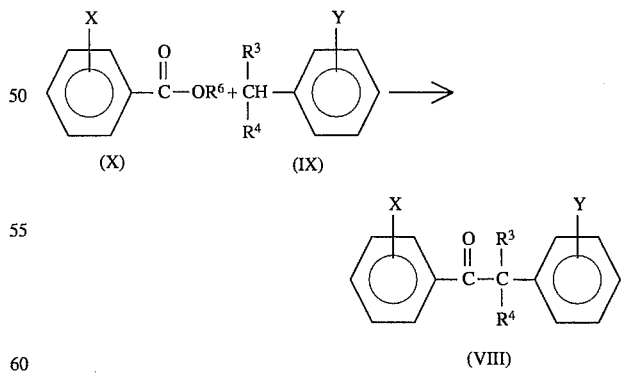

wherein $R^3$, $R^4$, X and Y have the same meanings as those defined above, and $R^6$ is a lower alkyl group.

That is, a compound of the general formula (VIII) can be produced by condensation reaction of a benzoic acid ester of the general formula (X) with a compound of the general formula (IX) in the presence of an inert solvent and a base.

The compound of the general formula (VI) can be produced, for example, by the production process illustrated below.

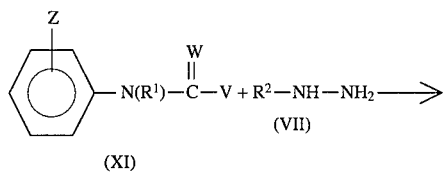

(XI)

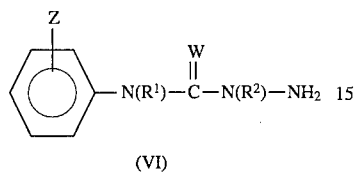

(VI)

wherein $R^1$, $R^2$, Z and W have the same meanings as those defined above, and V is a halogen atom or a leaving group such as a lower alkoxy group or an imidazole group.

That is, a compound of the general formula (VI) can be produced by reacting a compound of the general formula (XI) with a hydrazine derivative of the general formula (VII) in the presence of an inert solvent and a base.

Typical examples of the present invention are described below but should not be construed as limiting the scope of the invention.

EXAMPLE 1

1-1. Production of benzyl phenyl ketone hydrazone (compound No. V-1)

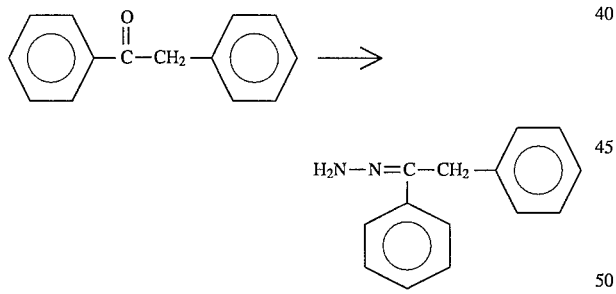

In 100 ml of ethanol was dissolved 5.0 g (26 mmoles) of benzyl phenyl ketone, followed by adding thereto 20 ml of hydrazine hydrate, and the reaction was carried out with stirring at a reaction temperature of 30° to 40° C. for 6 hours.

After completion of the reaction, the solvent was removed by distillation under reduced pressure from the reaction solution containing the desired compound, and the residue was purified by a silica gel column chromatography (eluent, ethyl acetate: n-hexane=1:4) to obtain 3.7 g of the desired compound as crystals.

Physical properties: m.p. 55° C. Yield: 69%.

1-2. Production of 2-(1,2-diphenylethylidene)-N-phenyl-hydrazinecarboxamide (compound No. A001)

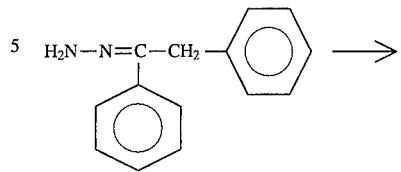

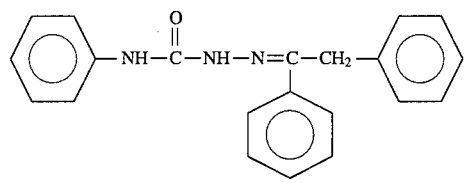

In 30 ml of tetrahydrofuran was dissolved 0.50 g (2.4 mmoles) of benzyl phenyl ketone hydrazone, followed by adding thereto 0.5 ml of triethylamine and 0.28 g (2.4 mmoles) of phenyl isocyanate, and the reaction was carried out at room temperature for 3 hours.

After completion of the reaction, the reaction solution containing the desired compound was concentrated under reduced pressure, and the residue was purified by a silica gel column chromatography (eluent, chloroform) to obtain 0.47 g of the desired compound as crystals. Physical properties: m.p. 181° C. Yield: 60%.

EXAMPLE 2

Production of N-(4-chlorophenyl)-2-(1,2diphenylethylidene) hydrazinecarboxamide (compound No. A004)

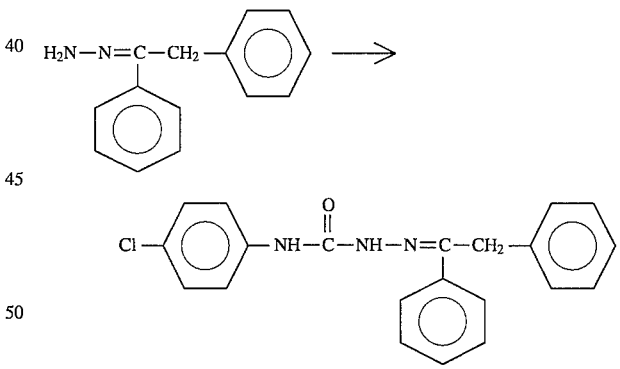

In 30 ml of tetrahydrofuran was dissolved 0.62 g (3.0 mmoles) of benzyl phenyl ketone hydrazone, followed by adding thereto a drop of triethylamine and 0.45 g (3.0 mmoles) of 4-chlorophenyl isocyanate, and the reaction was carried out at room temperature for 3 hours.

After completion of the reaction, the solvent was removed by distillation under reduced pressure from the reaction solution containing the desired compound, and the crude crystals precipitated were washed with ether to obtain 0.90 g of the desired compound as crystals.

Physical properties: m.p. 199° C. Yield: 84%.

EXAMPLE 3

3-1. Production of 4-fluorobenzylphenyl ketone hydrazone (compound No. V-2)

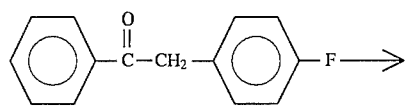

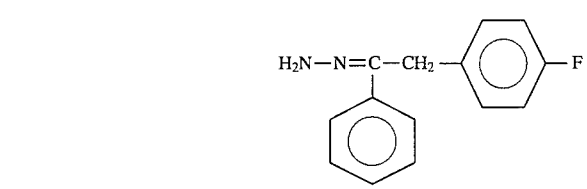

In 50 ml of ethanol was dissolved 3.0 g (14 mmoles) of 4-fluorobenzylphenyl ketone, followed by adding thereto 3 ml of hydrazine hydrate and 10 mg of p-toluenesulfonic acid, and the reaction was carried out with heating under reflux for 2 hours.

After completion of the reaction, the excess hydrazine hydrate and the ethanol were distilled off under reduced pressure. Water was added to the residue and the desired compound was extracted with ether. The ether layer was washed with water and dried over anhydrous magnesium sulfate, after which the ether was removed to obtain 3.0 g of the desired compound as paste.

Physical properties: paste. Yield: 93%.

3-2. Production of N-(4-chlorophenyl)-2-[2-(4-fluorophenyl)-1-phenylethylidene]hydrazinecarboxamide (compound No. A029)

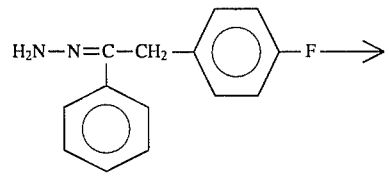

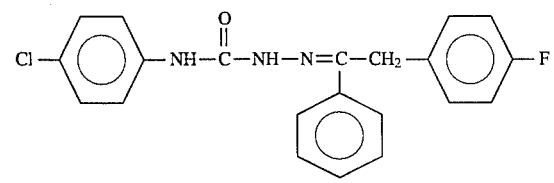

In 50 ml of tetrahydrofuran was dissolved 0.80 g (3.5 mmoles) of 4-fluorobenzylphenyl ketone hydrazone, followed by adding thereto 0.53 g (3.5 mmoles) of 4-chlorophenyl isocyanate, and the reaction was carried out at room temperature for 3 hours.

After completion of the reaction, the reaction solution containing the desired compound was concentrated under reduced pressure, and the residue was purified by a silica gel column chromatography (eluent, chloroform) to obtain 0.9 g of the desired compound as crystals. Physical properties: m.p. 213° C. Yield: 68%.

EXAMPLE 4

4-1. Production of 4-cyanobenzylphenyl ketone hydrazone (compound No. V-3)

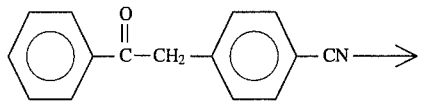

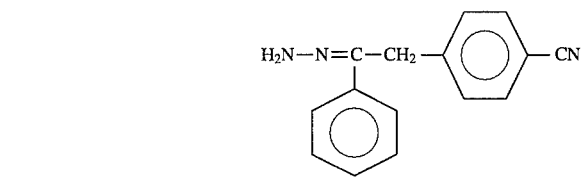

In 200 ml of ethanol was dissolved 5.0 g (24 mmoles) of 4-cyanobenzylphenyl ketone, followed by adding thereto 15 ml of hydrazine hydrate and 15 mg of p-toluenesulfonic acid, and the reaction was carried out with heating under reflux for 4 hours.

After completion of the reaction, the excess hydrazine hydrate and the ethanol were distilled off under reduced pressure. Water was added to the residue and the desired compound was extracted with ether. The ether layer was washed with water and dried over anhydrous magnesium sulfate, after which the ether was removed to obtain 4.4 g of the desired compound as crystals.

Physical properties: m.p. 91° C. Yield: 83%.

4-2. Production of 2-[2-(4-cyanophenyl)-1-phenylethylidene]-N-(4-trifluoromethylphenyl)hydrazinecarboxamide (compound No. A050)

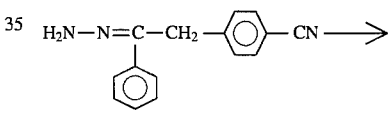

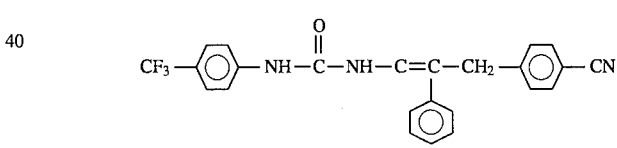

In 30 ml of tetrahydrofuran was dissolved 1.0 g (4.4 mmoles) of 4-cyanobenzylphenyl ketone hydrazone, followed by adding thereto 0.81 g (4.0 mmoles) of 4-trifluoromethylphenyl isocyanate, and the reaction was carried out at room temperature for 2 hours.

After completion of the reaction, the reaction solution containing the desired compound was concentrated under reduced pressure, and the residue was purified by a silica gel column chromatography (eluent, chloroform) to obtain 0.85 g of the desired compound as crystals.

Physical properties: m.p. 217° C. Yield: 50%.

EXAMPLE 5

5-1. Production of 4-nitrobenzylphenyl ketone hydrazone (compound No. V-4)

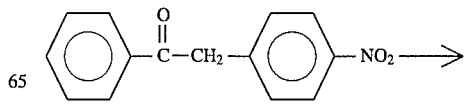

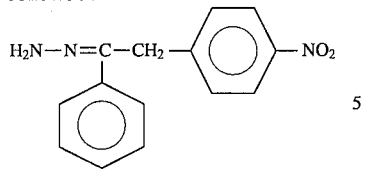

In 300 ml of ethanol was dissolved 5.0 g (21 mmoles) of 4-nitrobenzylphenyl ketone, followed by adding thereto 10 ml of hydrazine hydrate and 20 mg of p-toluenesulfonic acid, and the reaction was carried out at 60° C. for 2 hours.

After completion of the reaction, the excess hydrazine hydrate and the ethanol were distilled off under reduced pressure. Water was added to the residue and the desired compound was extracted with ethyl acetate. The ethyl acetate layer was washed with water and dried over anhydrous magnesium sulfate, after which the ethyl acetate was removed to obtain 4.9 g of the desired compound as crystals.

Physical properties: m.p. 72° C. Yield: 93%.

5-2. Production of 2-[2-(4-nitrophenyl)-1-phenylethylidene]-N-(4-trifluoromethoxyphenyl)hydrazinecarbothioamide (compound No. A080)

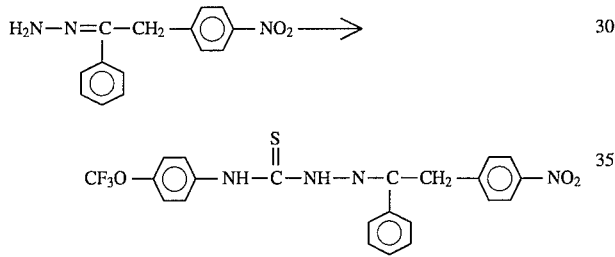

In 30 ml of tetrahydrofuran was dissolved 0.80 g (3.1 mmoles) of 4-nitrobenzylphenyl ketone hydrazone, followed by adding thereto 0.62 g (2.8 mmoles) of -trifluoromethoxyphenyl isothiocyanate and three drops of triethylamine, and the reaction was carried out with heating under reflux for 5 hours. After completion of the reaction, the reaction solution containing the desired compound was concentrated under reduced pressure, and the residue was purified by a silica gel column chromatography (eluent, chloroform) to obtain 0.65 g of the desired compound as crystals.

Physical properties: m.p. 139° C. Yield: 49%.

EXAMPLE 6

6-1. Production of 4-fluorobenzyl-4-fluorophenyl-ketone hydrazone (compound No. V-5)

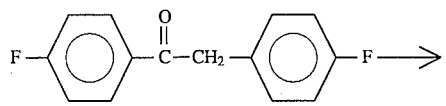

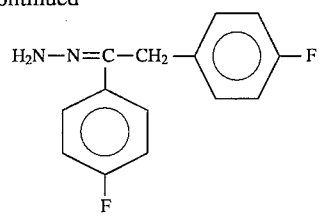

In 50 ml of ethanol was dissolved 4.0 g (17 mmoles) of 4-fluorobenzyl-4-fluorophenylketone, followed by adding thereto 10 ml of hydrazine hydrate and a drop of concentrated sulfuric acid, and the reaction was carried out with heating under reflux for 2 hours.

After completion of the reaction the excess hydrazine hydrate and ethanol were distilled off under reduced pressure. Water was added to the residue and the desired compound was extracted with ether. The ether layer was washed with water and dried over anhydrous magnesium sulfate, after which the ether was removed under reduced pressure to obtain 4.2 g of the desired compound as paste.

Physical properties: paste. Yield: 100%.

6.2. Production of 2-[1,2-bis(4-fluorophenyl)ethylidene]-N-(4-trifluoromethylphenyl) hydrazinecarboxamide (compound No. A227)

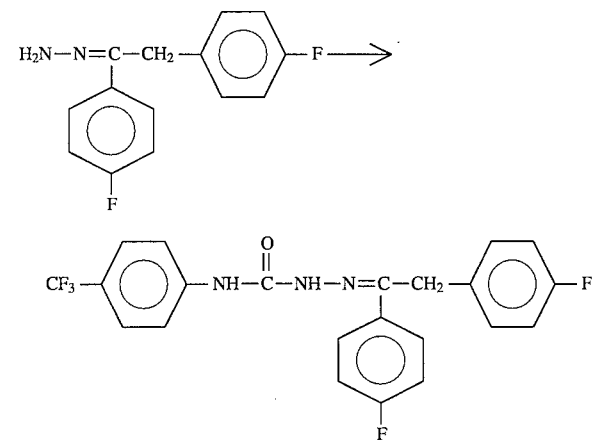

In a mixture of 15 ml of pyridine and 15 ml of tetrahydrofuran was dissolved 0.50 g (2.0 mmoles) of 4-fluorobenzyl-4-fluorophenylketone hydrazone, followed by adding thereto 0.38 g (2.0 mmoles) of 4-trifluoromethylphenyl isocyanate, and the reaction was carried out at room temperature for 4 hours.

After completion of the reaction, the solvent was distilled off under reduced pressure and the residue was washed with an ether-n-hexane mixed solvent, whereby 0.55 g of the desired compound was obtained as crystals.

Physical properties: m.p. 199° C. Yield: 63%.

EXAMPLE 7

Production of 2-(1,2-diphenylethylidene)-N-methyl-N-phenylhydrazinecarboxamide (compound No. A300)

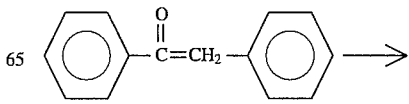

57
-continued

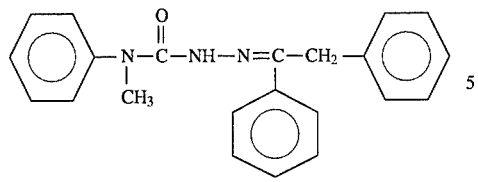

In 30 ml of ethanol were dissolved 0.65 g (3.3 mmoles) of benzyl phenyl ketone and N-methyl-N-phenylhydrazinecarboxamide, followed by adding thereto a drop of concentrated sulfuric acid, and the reaction was carried out with heating under reflux for 8 hours. After completion of the reaction, the solvent was distilled off under reduced pressure, and the residue was purified by a silica gel column chromatography (eluent, ethyl acetate: n-hexane=3:2) to obtain 0.26 g of the desired compound as crystals.

Physical properties: m.p. 113° C. Yield: 23%.

EXAMPLE 8

Production of 2-(1,2-diphenylethylidene)-1-methyl-N-phenylhydrazinecarboxamide (compound No. A303)

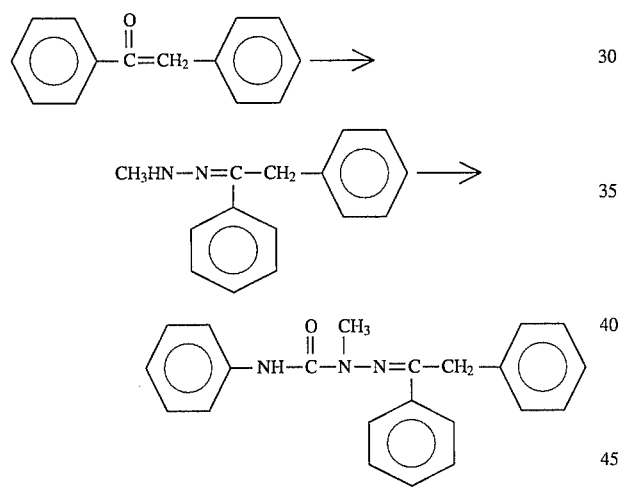

In 50 ml of toluene was dissolved 1.0 g (5.1 mmoles) of benzyl phenyl ketone, followed by adding thereto 0.50 g (11 mmoles) of methylhydrazine and 0.20 g (1.2 mmoles) of p-toluenesulfonic acid, and the reaction was carried out with heating under reflux for 4 hours while eliminating water from the reaction system by azeotropy by means of a Dean-Stark trap.

After completion of the reaction, the solvent was distilled off under reduced pressure and the oil thus obtained was dissolved in 20 ml of tetrahydrofuran, followed by adding thereto 0.58 g (4.9 mmoles) of phenyl isocyanate and 0.5 ml of triethylamine. The resulting mixture was allowed to stand overnight at room temperature to be subjected to reaction.

After completion of the reaction, and the residue was purified by a silica gel column chromatography (eluent, ethyl acetate: n-hexane=1:5) to obtain 0.76 g of the desired compound as crystals.

Physical properties: m.p. 111° C. Yield: 46%.

58
EXAMPLE 9

9-1. Production of benzoin hydrazone (compound No. V-6)

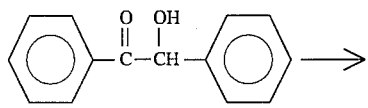

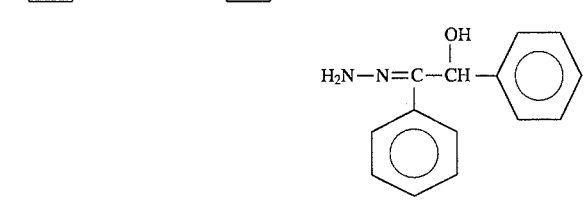

In 50 ml of ethanol were dissolved 5.0 g (24 mmoles) of benzoin and 10 ml of hydrazine hydrate, followed by adding thereto a drop of concentrated sulfuric acid, and the reaction was carried out with heating under reflux for 2 hours.

After completion of the reaction, the excess hydrazine hydrate and ethanol were distilled off under reduced pressure. Water was added to the residue and the desired compound was extracted with ether. The ether layer was washed with water and dried over anhydrous magnesium sulfate, after which the ether was to obtain 5.1 g of the desired compound as paste.

Physical properties: paste. Yield: 96%.

9-2. Production of 2-(2-hydroxy-1,2-diphenylethylidene)-N-phenylhydrazinecarboxamide (compound No. A330)

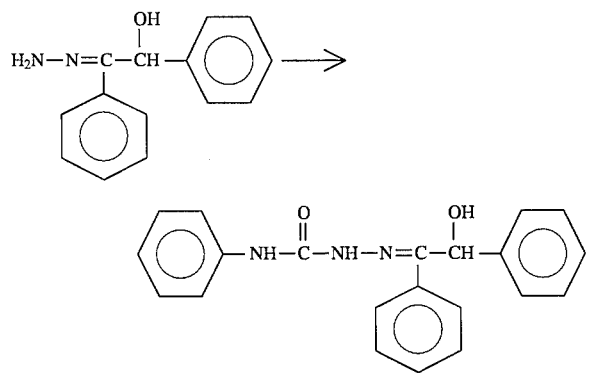

In 30 ml of tetrahydrofuran was dissolved 0.80 g (3.5 mmoles) of benzoin hydrazone, followed by adding thereto 0.42 g (3.5 mmoles) of phenyl isocyanate, and the reaction was carried out at room temperature for 4 hours.

After completion of the reaction, the solvent was distilled off under reduced pressure, and the residue was purified by a silica gel colume chromatography (eluent, tetrahydrofuran: chloroform=1:10) to obtain 0.70 g of the desired compound as crystals.

Physical properties: m.p. 167° C. Yield: 57%.

EXAMPLE 10

Production of 2-[2-(4-cyanophenyl)-1-phenylethyl]-N-(4-trifluoromethoxyphenyl)hydrazinecarboxamine (compound No. B006)

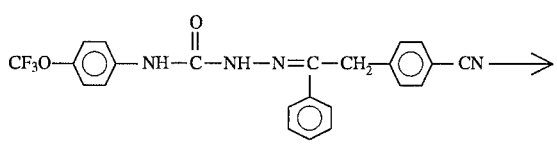

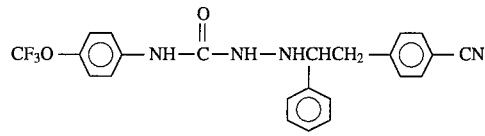

10-1.

In a mixture of 20 ml of tetrahydrofuran and 30 ml of methanol was dissolved 0.70 g (1.6 mmoles) of 2-[2-(4-cyanophenyl)-1-phenylethylidene]-N-(4-trifluorometh oxyphenyl)hydrazinecarboxamide, and 0.20 g (3.2 mmoles) of sodium cyanoborohydride was added to the solution. A saturated solution of hydrogen chloride in methanol was added dropwise with stirring at room temperature, and the reaction was carried out at room temperature for 1 hour.

After completion of the reaction, the solvent was distilled off under reduced pressure and ethyl acetate was added to the residue. The resulting mixture was neutralized with an aqueous sodium hydrogencarbonate solution and the ethyl acetate layer was separated. The thus obtained ethyl acetate containing the desired compound was dried over anhydrous magnedium sulfate, and the solvent was removed to obtain crude crystals of the desired compound.

The crude crystals obtained were washed with ether to obtain 0.54 g of the desired compound as crystals.

Physical properties: m.p. 204° C. Yield: 77%.

10-2.

In 80 ml of tetrahydrofuran was dissolved 1.0 g (2.3 mmoles) of 2-[2-(4-cyanophenyl)-1-phenylethylidene]-N-(4-trifluoromethoxyphenyl) hydrazinecarboxamide, and 0.1 g of 5% palladium carbon was added to the solution. The resulting mixture was allowed to absorb hydrogen gas at a pressure of 6 kg/cm² under shaking at room temperature for 60 hours.

After completion of the reaction, the catalyst was filtered off and the filtrate was evaporated under reduced pressure to obtain crude crystals of the desired compound.

The crude crystals obtained were washed with an ether-n-hexane mixture to obtain 0.97 g of the desired compound as crystals.

Physical properties: m.p. 204° C. Yield: 97%.

EXAMPLE 11

Production of 2-[2-(4-nitrophenyl)-1-phenylethyl]-N-(4-trifluoromethoxyphenyl) hydrazinecarboxamide (compound No. B008)

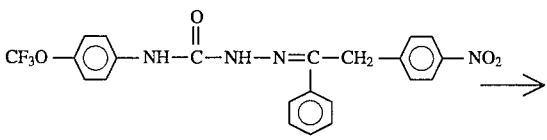

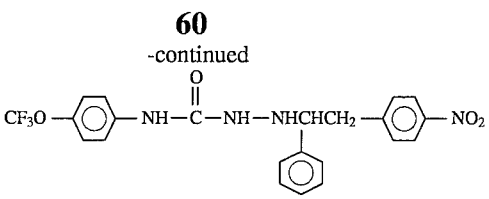

In a mixture of 10 ml of tetrahydrofuran and 10 ml of methanol was dissolved 0.48 g (1.0 mmole) of 2-[2-(4-nitrophenyl)-1-phenylethylidene]-N-(4-trifluorometh oxyphenyl)hydrazinecarboxamide, and 0.07 g (1 mmole) of sodium cyanoborohydride was added to the solution. Then, 5 ml of a saturated solution of hydrogen chloride in methanol was added dropwise with ice-cooling and the reaction was carried out for 30 minutes.

After completion of the reaction, the solvent was distilled off under reduced pressure and ethyl acetate was added to the residue. The resulting mixture was neutralized with an aqueous sodium hydrogencarbonate solution and the ethyl acetate layer was separated. The thus obtained ethyl acetate containing the desired compound was dried over anhydrous magnesium sulfate, and the solvent was removed to obtain crude crystals of the desired compound.

The crude crystals obtained were washed with ether-n-hexane to obtain 0.36 g of the desired compound as crystals.

Physical properties: m.p. 188° C. Yield: 75%.

EXAMPLE 12

Production of 2-[1-(4-chlorophenyl)-2-(4-cyanophenyl) ethyl-N-(4-trifluoromethoxyphenyl)hydra-zinecarbothioamide (compound No. B033)

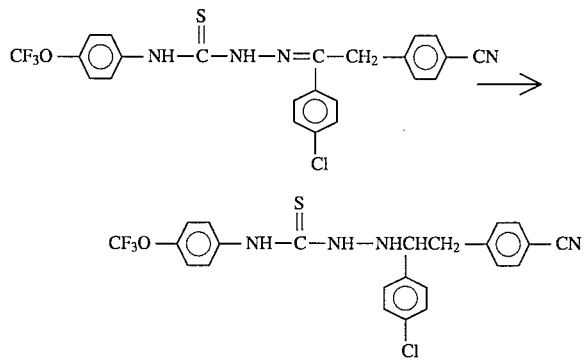

In a mixture of 10 ml of tetrahydrofuran and 30 ml of methanol was dissolved 0.50 g (1.0 mmole) of 2-[1-(4-chlorophenyl)-2-(4-cyanophenyl)ethylidene]-N-(4-trifluoromethoxyphenyl) hydrazinecarbothioamide, and 0.19 g (3.1 mmoles) of sodium cyanoborohydride was added to the solution. Then, 5 ml of a saturated solution of hydrogen chloride in methanol was added dropwise at room temperature, and the reaction was carried out for 2 hours.

After completion of the reaction, the solvent was distilled off under reduced pressure and the ethyl acetate was added to the residue. The resulting mixture was neutralized with an aqueous sodium hydrogencarbonate solution and the ethyl acetate layer was separated. The thus obtained ethyl acetate containing the desired compound was dried over anhydrous magnesium sulfate, and the solvent was removed to obtain crude crystals of the desired compound.

The crude crystals obtained were washed with ether-n-hexane to obtain 0.27 g of the desired compound as crystals.

Physical properties: m.p. 195° C. Yield: 54%.

EXAMPLE 13

Production of 2-acetyl-2-[1-(3-chlorophenyl)-2-(4-cyanophenyl) ethyl]-N-(4-trifluoromethoxyphenyl)hydrazinecarboxamide (compound No. B035)

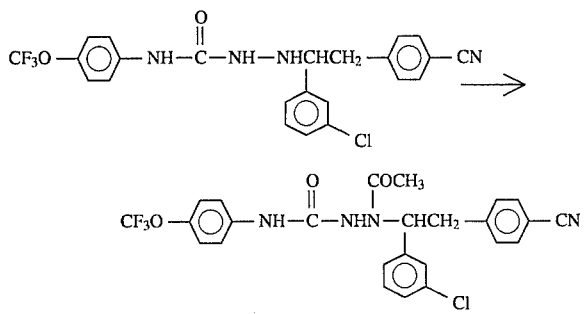

In 30 ml of tetrahydrofuran was dissolved 0.70 g (1.5 mmoles) of 2-[1-(3-chlorophenyl)-2-(4-cyanophenyl)ethyl] -N-(4-trifluoromethoxyphenyl)hydrazinecarboxamide obtained in the same manner as in Example 10. To the resulting solution were added 0.35 g (4.4 mmoles) of acetyl chloride and 45 g (4.4 mmoles) of triethylamine at room temperature, and the reaction was carried out for 2 hours.

After completion of the reaction, the solvent was distilled off under reduced pressure, water was added to the residue and the desired compound was extracted with ethyl acetate. The ethyl acetate layer was washed with water and dried over anhydrous magnesium sulfate. The solvent was removed to obtain crude crystals of the desired compound.

The crude crystals obtained were washed with ether to obtain 0.55 g of the desired compound as crystals.

Physical properties: m.p. 178° C. Yield: 54%.

EXAMPLE 14

Production of 2-[2-(4-cyanophenyl)-1-(3-trifluoromethylphenyl) ethylidene]-N-(4-trifluoromethoxyphenyl)hydrazinecarboxamide (compound No. A261)

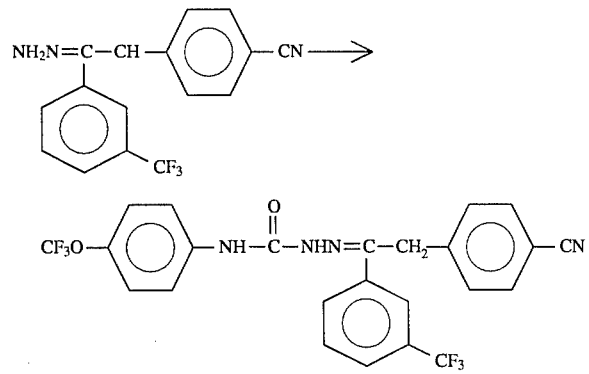

In 30 ml of tetrahydrofuran was dissolved 0.50 g (1.7 mmoles) of 4-cyanobenzyl-3-trifluoromethylphenylketone hydrazone, and 1 ml of pyridine was added. Then, a solution prepared by diluting 0.32 g (1.6 mmoles) of 4-trifluoromethoxyphenyl isocyanate with 5 ml of tetrahydrofuran was added dropwise with stirring at room temperature. After completion of the dropwise addition, the reaction was carried out at room temperature for another 4 hours.

After completion of the reaction, the solvent was distilled off under reduced pressure, and crude crystals obtained was washed with ether-n-hexane to obtain 0.40 g of the desired compound as crystals.

Physical properties: m.p. 191° C. Yield: 40%.

Insecticides containing the hydrazinecarboxamide derivative of the general formula (I) of the present invention as an active ingredient are suitable for controlling various insect pests such as agricultural insect pests, forest insect pests, horticultural insect pests, stored grain insect pests, sanitary insect pests, nematodes, etc. They have an insecticidal effect also, for example, on LEPIDOPTERA including summer fruit torrix (*Adoxophyes orana fasciata*), smaller tea tortrix (*Adoxophyes sp.*), Manchurian fruit moth (*Grapholita inopinata*), oriental fruit moth (*Grapholita mlesta*), soybean pod border (*Leguminivora glycinivorella*), mulberry leafroller (*Olethreutes mori*), tea leafroller (*Caloptilla thevivora*), *Caloptilia sp.* (*Caloptilia zachrysa*), apple leafminer (*Phyllonorycter ringoniella*), pear barkminer (*Spulerina astaurota*), common white (*Piers rapae crucivora*), tabacco budworm (*Heliothis armigera*), clodling moth (*Laspeyresia pomonella*), diamondback moth (*Plutella xylostella*), apple fruit moth (*Argyresthia conjugella*), peach fruit moth (*Carposina niponensis*), rice stem borer (*Chilo suppressalia*), rice leafroller (*Cnaphalocrocis medinails*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnip aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), San Jose scale (*Comstockaspis perniciosa*), arrowhead scale (*Unaspis yanonensis*), etc.; COLEOPTERA including soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintioctopunctata*), adzuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Outlema oryzae*), striped flea beetle (*Phyllotreta striolata*), pine shoot beetle (*Tomicus piniperda*), Colorade potato beetle (*Leptinotarsa decemilineata*), Mexican bean beetle (*Epilachna varivestis*), corn rootworm (*Diabrotica sp.*), etc.: DIPTERA including melon fly (*Dacus(Zeugodacus) cucurbitae*), oriental fruit fly (*Dacus(Bactrocera) dorsalis*), rice leafminer (*Agromyza oryzae*), onion maggot (*Delia antiqua*), seedcorn maggot (*Delia platura*), soybean pod gall midge (*Asphodylia sp.*), muscid fly (*Musca domestica*), house mosquite (*Culex piplens*), etc.; and TYLENCHIDA including root-lesion nematode (*Pratylenchus sp.*), coffer root-lesion nematode (*Pratylenchus coffeae*), potato cyst nematode (*Globodera rostochiensis*), root-knot nematode (*meloidogyne sp.*), citrus nematode (*Tylenchulus semipenetrans*), *Aphelenchus sp.* (*Aphelenchus avenae*), chrysanthemum foliar nematode (*Aphelenchoides ritzemabosi*), etc. The insecticides are markedly effective particularly against insect pests belonging to LEPIDOPTERA, COLEOPTERA and the like.

The zoological names and the like are in accordance with Applied Zoology and Entomology Society of Japan, "List of Agricultural and Forest Injurious Animals and Insects", published in 1987.

The agricultural and horticultural insecticide of the present invention has a marked insecticidal effect on the above-exemplified insect pests, sanitary insect pests, and/or nematodes, which are injurious to paddy fields, fruit trees, vegetables and other crops, and flowers and ornament plants. Therefore, the desired effect of the insecticide of the present invention can be obtained by applying the insecticide to the paddy field water, stalks and leaves of fruit trees, vegetables, other crops, flowers and ornament plants, soil, etc., or to the inside of a house or ditches around a house, in which the above-exemplified sanitary insect pests injurious to men and beasts appear or are expected to appear. The application is carried out at a season at which the insect pests, sanitary insect pests or nematodes are expected to appear, before their appearance or at the time when their appearance is confirmed.

This invention however should not be limited to these embodiments.

When the hydrazinecarboxamide derivative of the general formula (I) of this invention is used as an insecticide, it is generally prepared into conveniently usable forms according to an ordinary manner for preparation of agrochemicals.

That is, the hydrazinecarboxamide derivative of the general formula (I) of this invention and, optionally, an adjuvant are blended with a suitable inert carrier in a proper proportion and prepared into a suitable preparation form such as a suspension, emulsifiable concentrate, soluble concentrate, wettable powder, granules, dust or tablet through dissolution, dispersion, suspension, mixing, impregnation, adsorption or sticking.

The inert carrier in this invention may be solid or liquid. Examples of the solid carrier are soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes [e.g. diatomaceous earth, silica sand, mica and white carbon, i.e. synthetic, high-dispersion silicic acid, also called finely divided hydrated silica or hydrated silicic acid, some of commercially available products contain silicate as the major component)], activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalene; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. Examples of the surfactant are polyoxyethylene alkyl ethers, polyoxyethylenealkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, an adjuvant may be used. Examples of such an adjuvant are casein, gelatin, starch, methylcellulose, carboxymethylcellulose, gum arabic, polyvinyl alcohol, turpentine, bran oil, bentonite and ligninsulfonates.

To improve the flowability of a solid product, an adjuvant may be used. Examples of such an adjuvant are waxes, stearates and alkyl phosphates.

Adjuvants such as naphthalenesulfonic acid condensation products and polycondensates of phosphates may be used as a peptizer for dispersible products.

Adjuvants, e.g. silicon oils may be also used as a defoaming agent.

The content of the active ingredient may be varied as required. In dusts or granules, the suitable content thereof is from 0.01 to 50% by weight. In emulsifiable concentrates, flowable wettable powders, it is also from 0.01 to 50% by weight.

An insecticide containing the hydrazinecarboxamide derivative of the general formula (I) of this invention as an active ingredient is used to control a variety of insect pests in the following manner. That is, it is applied to the insect pests or a site where appearance of growth of the insect pests is undesirable, as it is or after being properly diluted with or suspended in water or the like, in an amount effective for control of the insect pests.

The amount of the insecticide containing the hydrazinecarboxamide derivative of the general formula (I) of this invention as an active ingredient is varied depending upon various factors such as a purpose, insect pests to be controlled, a growth state of a plant, tendency of insect pests appearance, weather, environmental conditions, a preparation form, an application method, an application site and an application time. It may be properly chosen in the range of 0.1 g to 5 kg (in terms of the active ingredient) per 10 ares depending upon purposes.

The insecticide containing the hydrozinecarboxamide derivative of the general formula (I) of this invention as an active ingredient may be used in admixture with other insecticides or fungicides in order to expand both spectrum of controllable insect pest species and the period of time when effective applications are possible or to reduce the dosage.

Typical preparation examples and test examples of the present invention are described below but should not be construed as limiting the scope of the invention.

In the preparation examples, parts are all by weight.

FORMULATION EXAMPLE 1

| | |
|---|---|
| Each compound of the invention | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

FORMULATION EXAMPLE 2

| | |
|---|---|
| Each compound of the invention | 3 parts |
| Clay powder | 82 parts |
| Diatomaceous earth powder | 15 parts |

A dust was prepared by mixing uniformly and grinding the above ingredients.

FORMULATION EXAMPLE 3

| | |
|---|---|
| Each compound of the invention | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

FORMULATION EXAMPLE 4

| | |
|---|---|
| Each compound of the invention | 20 parts |
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

TEST EXAMPLE 1

Insecticidal effect on common cutworm (*Spodoptera litura*)

A piece of cabbage leaf (cultivar: Shikidori) was immersed for about 30 seconds in a liquid chemical prepared by diluting a preparation containing each compound of this invention as an active ingredient to adjust the concentration to 500 ppm. After air-drying, it was placed in a plastic Petri dish having a diameter of 9 cm, and inoculated with second-instar larvae of common cutworm, after which the dish was closed and then allowed to stand in a room thermostated at 25° C. Eight days after the inoculation, the dead and alive were counted. The mortality was calculated according to the following equation and judgement was passed according to the criterion shown below. The test was carried out with triplicate groups of 10 insects.

$$\text{Corrected mortality (\%)} = \left( \frac{\text{Number of dead larvae}}{\text{Number of inoculated larvae}} \right) \times 100$$

Criterion:

| Degree of insecticidal effect | Mortality (%) |
|---|---|
| A | 100 |
| B | 99–90 |
| C | 89–80 |
| D | 79–50 |
| E | Less than 49 |

The results obtained are shown in Table 7.

TABLE 7

| Compound No. | Concentration (ppm) | Judgement |
|---|---|---|
| A007 | 500 | A |
| A016 | 500 | C |
| A017 | 500 | D |
| A018 | 500 | A |
| A019 | 500 | C |
| A020 | 500 | A |
| A025 | 500 | D |
| A027 | 500 | A |
| A028 | 500 | A |
| A033 | 500 | A |
| A034 | 500 | A |
| A038 | 500 | A |
| A042 | 500 | A |
| A049 | 500 | C |
| A050 | 500 | C |
| A051 | 500 | A |
| A054 | 500 | A |
| A055 | 500 | A |
| A056 | 500 | A |
| A057 | 500 | A |
| A058 | 500 | A |
| A059 | 500 | A |
| A061 | 500 | A |
| A062 | 500 | A |
| A063 | 500 | A |
| A065 | 500 | A |
| A074 | 500 | D |
| A076 | 500 | A |
| A077 | 500 | A |
| A078 | 500 | A |
| A079 | 500 | A |
| A080 | 500 | A |
| A081 | 500 | A |
| A082 | 500 | A |
| A087 | 500 | A |
| A089 | 500 | A |
| A090 | 500 | A |
| A091 | 500 | A |
| A092 | 500 | A |
| A093 | 500 | A |
| A096 | 500 | A |
| A097 | 500 | A |
| A098 | 500 | C |
| A099 | 500 | A |
| A101 | 500 | A |
| A105 | 500 | A |
| A106 | 500 | A |
| A109 | 500 | A |
| A111 | 500 | A |
| A112 | 500 | C |
| A113 | 500 | A |
| A114 | 500 | A |
| A115 | 500 | A |

TABLE 7-continued

| Compound No. | Concentration (ppm) | Judgement |
|---|---|---|
| A116 | 500 | A |
| A118 | 500 | D |
| A120 | 500 | D |
| A125 | 500 | A |
| A127 | 500 | A |
| A129 | 500 | A |
| A130 | 500 | A |
| A131 | 500 | A |
| A132 | 500 | A |
| A133 | 500 | A |
| A134 | 500 | D |
| A135 | 500 | A |
| A137 | 500 | A |
| A138 | 500 | A |
| A140 | 500 | A |
| A141 | 500 | A |
| A142 | 500 | A |
| A143 | 500 | D |
| A146 | 500 | A |
| A147 | 500 | A |
| A149 | 500 | A |
| A151 | 500 | A |
| A152 | 500 | A |
| A153 | 500 | A |
| A155 | 500 | A |
| A158 | 500 | A |
| A161 | 500 | A |
| A164 | 500 | A |
| A165 | 500 | A |
| A167 | 500 | A |
| A168 | 500 | A |
| A169 | 500 | A |
| A170 | 500 | A |
| A171 | 500 | A |
| A172 | 500 | A |
| A173 | 500 | A |
| A178 | 500 | A |
| A179 | 500 | A |
| A182 | 500 | D |
| A185 | 500 | A |
| A189 | 500 | A |
| A194 | 500 | A |
| A195 | 500 | A |
| A196 | 500 | A |
| A197 | 500 | A |
| A198 | 500 | A |
| A199 | 500 | A |
| A200 | 500 | A |
| A201 | 500 | A |
| A202 | 500 | A |
| A203 | 500 | A |
| A212 | 500 | C |
| A213 | 500 | A |
| A214 | 500 | C |
| A216 | 500 | A |
| A218 | 500 | A |
| A219 | 500 | A |
| A220 | 500 | A |
| A221 | 500 | A |
| A225 | 500 | A |
| A226 | 500 | A |
| A227 | 500 | A |
| A228 | 500 | A |
| A229 | 500 | A |
| A230 | 500 | C |
| A231 | 500 | A |
| A232 | 500 | A |
| A233 | 500 | A |
| A234 | 500 | A |
| A235 | 500 | A |
| A239 | 500 | A |
| A240 | 500 | A |
| A241 | 500 | A |
| A242 | 500 | A |
| A248 | 500 | A |
| A249 | 500 | D |
| A250 | 500 | A |
| A251 | 500 | A |
| A254 | 500 | D |
| A257 | 500 | A |
| A258 | 500 | C |
| A260 | 500 | A |
| A261 | 500 | A |
| A262 | 500 | A |
| A263 | 500 | A |
| A264 | 500 | A |
| A265 | 500 | A |
| A269 | 500 | A |
| A274 | 500 | A |
| A281 | 500 | A |
| A285 | 500 | A |
| A292 | 500 | C |
| A310 | 500 | A |
| A312 | 500 | A |
| A313 | 500 | A |
| A314 | 500 | C |
| A318 | 500 | D |
| A319 | 500 | A |
| A320 | 500 | A |
| A321 | 500 | A |
| A325 | 500 | C |
| A326 | 500 | A |
| A342 | 500 | D |
| A343 | 500 | A |
| A344 | 500 | A |
| A354 | 500 | D |
| A362 | 500 | A |
| A367 | 500 | A |
| A378 | 500 | A |
| A381 | 500 | A |
| A383 | 500 | A |
| A385 | 500 | A |
| A386 | 500 | A |
| A388 | 500 | C |
| A389 | 500 | A |
| A390 | 500 | C |
| A393 | 500 | A |
| A394 | 500 | C |
| A395 | 500 | A |
| A397 | 500 | A |
| A398 | 500 | C |
| A399 | 500 | C |
| A400 | 500 | A |
| A401 | 500 | A |
| A402 | 500 | A |
| A403 | 500 | A |
| A404 | 500 | A |
| A405 | 500 | A |
| A406 | 500 | A |
| A409 | 500 | A |
| A410 | 500 | A |
| A411 | 500 | A |
| A412 | 500 | A |
| A415 | 500 | A |
| A418 | 500 | A |
| A419 | 500 | A |
| A420 | 500 | A |
| A421 | 500 | A |
| A422 | 500 | A |
| A423 | 500 | A |
| A424 | 500 | A |
| A425 | 500 | A |
| A426 | 500 | C |
| A427 | 500 | A |
| A428 | 500 | A |
| A429 | 500 | A |
| A430 | 500 | D |
| A431 | 500 | C |
| A432 | 500 | A |
| A433 | 500 | A |

TABLE 7-continued

| Compound No. | Concentration (ppm) | Judgement |
|---|---|---|
| A434 | 500 | C |
| A436 | 500 | A |
| A437 | 500 | A |
| A438 | 500 | D |
| A439 | 500 | A |
| A440 | 500 | A |
| A441 | 500 | A |
| A442 | 500 | A |
| A443 | 500 | A |
| A447 | 500 | A |
| A448 | 500 | A |
| A449 | 500 | A |
| A450 | 500 | A |
| A451 | 500 | A |
| A452 | 500 | A |
| A453 | 500 | D |
| A454 | 500 | A |
| A456 | 500 | D |
| A460 | 500 | A |
| A461 | 500 | A |
| A462 | 500 | A |
| A463 | 500 | A |
| A464 | 500 | A |
| A465 | 500 | A |
| A466 | 500 | D |
| A467 | 500 | A |
| A473 | 500 | D |
| A474 | 500 | C |
| A476 | 500 | A |
| A477 | 500 | A |
| A478 | 500 | A |
| A479 | 500 | A |
| A480 | 500 | D |
| B002 | 500 | A |
| B003 | 500 | A |
| B004 | 500 | A |
| B006 | 500 | A |
| B007 | 500 | A |
| B008 | 500 | A |
| B009 | 500 | A |
| B010 | 500 | A |
| B011 | 500 | A |
| B012 | 500 | A |
| B013 | 500 | A |
| B014 | 500 | A |
| B015 | 500 | A |
| B016 | 500 | A |
| B018 | 500 | A |
| B019 | 500 | A |
| B020 | 500 | A |
| B021 | 500 | A |
| B022 | 500 | D |
| B023 | 500 | A |
| B024 | 500 | A |
| B025 | 500 | A |
| B026 | 500 | A |
| B027 | 500 | D |
| B028 | 500 | A |
| B030 | 500 | A |
| B031 | 500 | A |
| B032 | 500 | A |
| B033 | 500 | A |
| B034 | 500 | A |
| B035 | 500 | A |
| B036 | 500 | A |
| B037 | 500 | C |
| B043 | 500 | A |
| B044 | 500 | A |
| B045 | 500 | A |
| B047 | 500 | D |
| B048 | 500 | A |
| B049 | 500 | A |
| B050 | 500 | A |
| B051 | 500 | A |
| B052 | 500 | A |
| B053 | 500 | A |
| B054 | 500 | C |
| B056 | 500 | A |
| B057 | 500 | A |
| B059 | 500 | D |
| B060 | 500 | A |
| B061 | 500 | D |
| B062 | 500 | A |
| B063 | 500 | A |
| B066 | 500 | A |
| B067 | 500 | A |
| B068 | 500 | A |
| B069 | 500 | A |
| B070 | 500 | A |
| B071 | 500 | A |
| B072 | 500 | A |
| B073 | 500 | A |
| B074 | 500 | A |
| B075 | 500 | A |
| B079 | 500 | A |
| B080 | 500 | A |
| B081 | 500 | A |
| B082 | 500 | A |
| B084 | 500 | D |
| B085 | 500 | A |
| B086 | 500 | A |
| B087 | 500 | A |
| B088 | 500 | A |
| B090 | 500 | A |
| B091 | 500 | A |
| B092 | 500 | A |
| B093 | 500 | A |
| B094 | 500 | A |
| B095 | 500 | A |
| B096 | 500 | A |
| B097 | 500 | C |
| B098 | 500 | A |
| B099 | 500 | A |
| B100 | 500 | A |
| B101 | 500 | A |
| B103 | 500 | A |
| B104 | 500 | A |
| B105 | 500 | A |
| B106 | 500 | D |
| B107 | 500 | A |
| B108 | 500 | A |
| B109 | 500 | A |
| B110 | 500 | A |
| B111 | 500 | A |
| B112 | 500 | A |
| B114 | 500 | A |
| B115 | 500 | A |
| B116 | 500 | A |
| B117 | 500 | A |
| B118 | 500 | A |
| B119 | 500 | A |
| B120 | 500 | A |
| B121 | 500 | A |
| B122 | 500 | A |
| B124 | 500 | A |
| B125 | 500 | A |
| B126 | 500 | A |
| B127 | 500 | A |
| B130 | 500 | A |
| B131 | 500 | D |
| B132 | 500 | A |
| B133 | 500 | A |
| B134 | 500 | A |
| B135 | 500 | A |
| B136 | 500 | A |
| B137 | 500 | A |
| B138 | 500 | A |
| B142 | 500 | A |
| B145 | 500 | A |

TEST EXAMPLE 2

Insecticidal effect on adult maize weevil (*Sitophilus zeamais*)

Twenty to thirty grains of the brown rice were immersed for about 30 seconds in a liquid chemical prepared by diluting a preparation containing each compound of this invention as an active ingredient to adjust the concentration to 200 ppm. After air-drying, they were placed in a glass Petri dish having a diameter of 4 cm, and inoculated with adult maize weevils, after which the dish was closed and then allowed to stand in a room thermostated at 25° C. Eight days after the inoculation, the dead and alive were counted. The mortality was calculated according to the equation described in Test Example 1 and judgement was passed according to the criterion shown in Test Example 1. The test was carried out with triplicate groups of 10 insects.

The results obtained are shown in Table 8.

TABLE 8

| Compound No. | Concentration (ppm) | Judgement |
|---|---|---|
| A004 | 200 | D |
| A006 | 200 | C |
| A007 | 200 | A |
| A015 | 200 | A |
| A016 | 200 | B |
| A017 | 200 | A |
| A018 | 200 | A |
| A020 | 200 | A |
| A021 | 200 | A |
| A026 | 200 | A |
| A027 | 200 | A |
| A028 | 200 | A |
| A029 | 200 | A |
| A030 | 200 | A |
| A033 | 200 | A |
| A038 | 200 | A |
| A040 | 200 | A |
| A042 | 200 | D |
| A044 | 200 | D |
| A046 | 200 | C |
| A050 | 200 | A |
| A056 | 200 | A |
| A057 | 200 | A |
| A058 | 200 | B |
| A059 | 200 | A |
| A061 | 200 | D |
| A062 | 200 | D |
| A067 | 200 | A |
| A073 | 200 | A |
| A077 | 200 | A |
| A078 | 200 | A |
| A079 | 200 | A |
| A080 | 200 | D |
| A081 | 200 | A |
| A082 | 200 | B |
| A091 | 200 | A |
| A092 | 200 | A |
| A093 | 200 | A |
| A096 | 200 | A |
| A097 | 200 | A |
| A098 | 200 | A |
| A099 | 200 | A |
| A101 | 200 | A |
| A102 | 200 | D |
| A103 | 200 | A |
| A105 | 200 | A |
| A106 | 200 | A |
| A110 | 200 | A |
| A111 | 200 | A |
| A112 | 200 | A |
| A113 | 200 | A |
| A114 | 200 | A |

TABLE 8-continued

| Compound No. | Concentration (ppm) | Judgement |
|---|---|---|
| A115 | 200 | C |
| A116 | 200 | A |
| A118 | 200 | A |
| A123 | 200 | B |
| A125 | 200 | A |
| A127 | 200 | A |
| A131 | 200 | A |
| A132 | 200 | A |
| A133 | 200 | A |
| A134 | 200 | A |
| A135 | 200 | A |
| A137 | 200 | A |
| A138 | 200 | A |
| A140 | 200 | A |
| A141 | 200 | D |
| A146 | 200 | A |
| A147 | 200 | A |
| A148 | 200 | A |
| A149 | 200 | A |
| A150 | 200 | B |
| A151 | 200 | A |
| A152 | 200 | D |
| A154 | 200 | A |
| A155 | 200 | A |
| A156 | 200 | A |
| A163 | 200 | C |
| A164 | 200 | A |
| A165 | 200 | A |
| A161 | 200 | D |
| A162 | 200 | D |
| A166 | 200 | C |
| A167 | 200 | B |
| A168 | 200 | A |
| A170 | 200 | A |
| A172 | 200 | D |
| A173 | 200 | C |
| A175 | 200 | D |
| A178 | 200 | A |
| A179 | 200 | B |
| A184 | 200 | A |
| A185 | 200 | A |
| A186 | 200 | C |
| A187 | 200 | C |
| A188 | 200 | D |
| A189 | 200 | A |
| A194 | 200 | A |
| A195 | 200 | A |
| A196 | 200 | A |
| A197 | 200 | A |
| A198 | 200 | A |
| A199 | 200 | A |
| A200 | 200 | A |
| A201 | 200 | A |
| A202 | 200 | A |
| A203 | 200 | A |
| A204 | 200 | A |
| A212 | 200 | D |
| A213 | 200 | D |
| A215 | 200 | A |
| A216 | 200 | A |
| A217 | 200 | A |
| A218 | 200 | A |
| A219 | 200 | A |
| A220 | 200 | A |
| A221 | 200 | A |
| A223 | 200 | A |
| A224 | 200 | A |
| A225 | 200 | A |
| A226 | 200 | A |
| A227 | 200 | A |
| A228 | 200 | A |
| A229 | 200 | A |
| A230 | 200 | B |
| A231 | 200 | A |

TABLE 8-continued

| Compound No. | Concentration (ppm) | Judgement |
|---|---|---|
| A232 | 200 | A |
| A233 | 200 | D |
| A234 | 200 | A |
| A235 | 200 | A |
| A236 | 200 | D |
| A237 | 200 | A |
| A238 | 200 | A |
| A239 | 200 | A |
| A240 | 200 | A |
| A241 | 200 | A |
| A242 | 200 | A |
| A257 | 200 | A |
| A258 | 200 | C |
| A259 | 200 | A |
| A260 | 200 | A |
| A261 | 200 | A |
| A262 | 200 | A |
| A263 | 200 | A |
| A264 | 200 | A |
| A265 | 200 | A |
| A268 | 200 | A |
| A269 | 200 | A |
| A270 | 200 | A |
| A272 | 200 | D |
| A273 | 200 | D |
| A283 | 200 | A |
| A284 | 200 | A |
| A285 | 200 | A |
| A288 | 200 | A |
| A289 | 200 | C |
| A292 | 200 | A |
| A293 | 200 | D |
| A294 | 200 | B |
| A295 | 200 | C |
| A319 | 200 | A |
| A320 | 200 | A |
| A321 | 200 | A |
| A326 | 200 | D |
| A351 | 200 | A |
| A370 | 200 | A |
| A374 | 200 | D |
| A380 | 200 | C |
| A381 | 200 | A |
| A383 | 200 | A |
| A385 | 200 | A |
| A386 | 200 | A |
| A388 | 200 | C |
| A389 | 200 | A |
| A390 | 200 | C |
| A393 | 200 | A |
| A394 | 200 | C |
| A395 | 200 | A |
| A397 | 200 | A |
| A398 | 200 | C |
| A400 | 200 | A |
| A401 | 200 | A |
| A402 | 200 | A |
| A403 | 200 | A |
| A404 | 200 | A |
| A405 | 200 | B |
| A406 | 200 | D |
| A409 | 200 | A |
| A410 | 200 | B |
| A411 | 200 | A |
| A415 | 200 | A |
| A418 | 200 | A |
| A419 | 200 | A |
| A420 | 200 | A |
| A421 | 200 | A |
| A422 | 200 | A |
| A423 | 200 | A |
| A424 | 200 | D |
| A425 | 200 | A |
| A427 | 200 | A |
| A429 | 200 | D |
| A430 | 200 | B |
| A436 | 200 | A |
| A439 | 200 | A |
| A440 | 200 | A |
| A441 | 200 | A |
| A442 | 200 | A |
| A443 | 200 | A |
| A447 | 200 | A |
| A448 | 200 | A |
| A449 | 200 | A |
| A450 | 200 | A |
| A451 | 200 | A |
| A452 | 200 | A |
| A453 | 200 | D |
| A454 | 200 | A |
| A460 | 200 | A |
| A461 | 200 | A |
| A462 | 200 | A |
| A463 | 200 | B |
| A464 | 200 | A |
| A465 | 200 | A |
| A466 | 200 | A |
| A467 | 200 | A |
| B001 | 200 | A |
| B002 | 200 | A |
| B003 | 200 | A |
| B004 | 200 | A |
| B006 | 200 | A |
| B008 | 200 | A |
| B009 | 200 | A |
| B010 | 200 | A |
| B011 | 200 | A |
| B012 | 200 | A |
| B013 | 200 | A |
| B014 | 200 | A |
| B015 | 200 | A |
| B016 | 200 | A |
| B018 | 200 | A |
| B019 | 200 | A |
| B020 | 200 | A |
| B021 | 200 | C |
| B022 | 200 | D |
| B023 | 200 | A |
| B024 | 200 | A |
| B025 | 200 | A |
| B026 | 200 | A |
| B028 | 200 | B |
| B031 | 200 | A |
| B032 | 200 | A |
| B034 | 200 | A |
| B035 | 200 | A |
| B036 | 200 | A |
| B037 | 200 | A |
| B044 | 200 | A |
| B045 | 200 | A |
| B047 | 200 | A |
| B048 | 200 | A |
| B049 | 200 | D |
| B050 | 200 | A |
| B051 | 200 | A |
| B052 | 200 | D |
| B055 | 200 | A |
| B056 | 200 | A |
| B057 | 200 | A |
| B060 | 200 | A |
| B061 | 200 | A |
| B062 | 200 | A |
| B063 | 200 | C |
| B066 | 200 | A |
| B067 | 200 | C |
| B068 | 200 | A |
| B069 | 200 | A |
| B070 | 200 | A |
| B071 | 200 | A |
| B072 | 200 | A |

TABLE 8-continued

| Compound No. | Concentration (ppm) | Judgement |
|---|---|---|
| B073 | 200 | A |
| B074 | 200 | A |
| B075 | 200 | A |
| B079 | 200 | A |
| B080 | 200 | A |
| B081 | 200 | A |
| B082 | 200 | A |
| B084 | 200 | A |
| B085 | 200 | A |
| B086 | 200 | B |
| B087 | 200 | A |
| B088 | 200 | B |
| B090 | 200 | A |
| B091 | 200 | B |
| B092 | 200 | A |
| B093 | 200 | A |
| B094 | 200 | A |
| B095 | 200 | A |
| B096 | 200 | A |
| B097 | 200 | C |
| B098 | 200 | B |
| B107 | 200 | A |
| B108 | 200 | A |
| B109 | 200 | A |
| B110 | 200 | A |
| B111 | 200 | A |
| B112 | 200 | A |
| B114 | 200 | A |
| B115 | 200 | A |
| B116 | 200 | A |
| B117 | 200 | A |
| B118 | 200 | A |
| B119 | 200 | A |
| B120 | 200 | A |
| B121 | 200 | A |
| B122 | 200 | A |
| B124 | 200 | A |
| B125 | 200 | A |
| B126 | 200 | A |
| B132 | 200 | A |
| B133 | 200 | A |
| B134 | 200 | A |
| B135 | 200 | A |
| B136 | 200 | A |
| B137 | 200 | A |
| B138 | 200 | A |
| B145 | 200 | A |

What is claimed is:

1. A hydrazinecarboxamide derivative represented by the general formula (I):

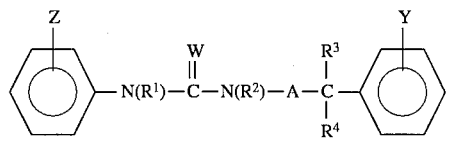

wherein $R^1$ is a hydrogen atom or a C1–3 alkyl group, $R^2$ is a hydrogen atom or a C1–3 alkyl group, $R^3$ is a hydrogen atom; a hydroxyl group; a C1–3 alkyl group; a C1–5 alkoxy group; a C1–3 alkylcarbonyloxy group; or an unsubstituted phenylcarbonyloxy group; $R^4$ is a hydrogen atom or a C1–3 alkyl group, $R^3$ and $R^4$ being able to be taken together to represent an oxygen atom, A is

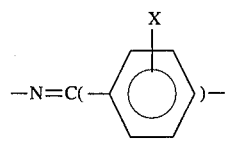

wherein X represents 1 to 5 atoms or groups which may be the same or different and are selected from the group consisting of hydrogen atom; hydroxyl group; halogen atoms; cyano group; C1–4 alkyl groups, C1–3 haloalkyl groups; C1–3 alkoxy groups, C1–3 haloalkoxy groups; C1–3 alkoxy C1–3 alkyl groups; C3–5 alkenyloxy groups; cyclo C3–6 alkylcarbonyloxy groups; C1–3 alkoxycarbonyloxy groups; C1–3 alkoxycarbonyl C1–3 alkyloxy groups; C1–3 alkylcarbonyl C1–3 alkyloxy groups; C1–3 alkylsulfonyloxy groups; phenoxy group; methylenedioxy group; alkenylene groups having 3 to 4 carbon atoms so as to form a polycyclic ring together with the adjacent carbon atom of the phenyl ring; substituted amino groups having as the substituent(s) 1 or 2 C1–3 alkyl groups which may be the same or different; substituted aminocarbonyloxy groups having as the substituent(s) 1 or 2 C1–3 alkyl groups which may be the same or different; Y represents 1 to 5 atoms or groups which may be the same or different and are selected from the group consisting of hydrogen atom; hydroxyl group; halogen atoms; cyano group; nitro group; C1–3 alkyl groups; C1–3 haloalkyl groups; C1–3 alkoxy groups; C1–3 haloalkoxy groups; C3–5 alkenyloxy groups; C1–3 alkylcarbonyloxy groups; C1–3 alkylsulfonyloxy groups; C1–3 haloalkylsulfonyloxy groups; C1–3 alkylthio groups; C1–3 haloalkylthio groups; C1–3 alkylsulfinyl groups; C1–3 haloalkylsulfinyl groups; C1–3 haloalkylsulfonyl groups; C1–3 alkoxycarbonyl groups; unsubstituted amino group; substituted amino groups having 1 or 2 substituents selected from the group consisting of formyl group, C1–3 alkylcarbonyl groups, C1–3 alkylsulfonyl groups, and substituted aminocarbonyl groups having as the substituent(s) one or more C1–3 alkyl groups which may be the same or different; unsubstituted aminocarbonyl group; substituted aminocabonyl groups having as the substituent(s) 1 or 2 C1–3 alkyl groups which may be the same or different; substituted aminosulfonyl groups having as the substituent(s) 1 or 2 C1–3 alkyl groups which may be the same or different; phenyl group; Z represents 1 to 5 atoms or groups which may be the same or different and are selected from the group consisting of halogen atoms; cyano group; nitro group; C1–6 alkyl groups; C1–3 haloalkyl groups; substituted C3–6 cycloalkyl groups having 1 to 5 substituents which may be the same or different and are selected from the group consisting of halogen atoms C1–5 alkoxy groups; C1–3 haloalkoxy groups; C1–3 alkylthio groups; C1–3 haloalkylthio groups; C1–3 alkylsulfinyl groups; C1–3 haloalkylsulfinyl groups; C1–3 alkylsulfonyl groups; C1–3 haloalkylsulfonyl groups; C1–3 alkylcarbonyl groups; C1–3 alkoxycarbonyl groups; C1–3 alkylcarbonyloxy groups; C1–3 alkylsulfonyloxy groups; C1–3 haloalkylsulfonyloxy groups; unsubstituted phenoxy group; substituted phenoxy groups having 1 to 5 substituents which may be the same or different and are selected from the group consisting of halogen atoms and C1–3 haloalkyl groups, unsubstituted pyridyloxy group; substituted pyridyloxy groups having as the substituent(s) 1 to 4 atoms or groups which may be the same or different and are selected from the group consisting of halogen atoms, and C1–3 haloalkyl groups, and W is an oxygen atom or a sulfur atom.

2. A hydrazinecarboxamide derivative according to claim 1, wherein $R^1$ is a hydrogen atom or a C1–3 alkyl group, $R^2$ is a hydrogen atom or a C1–3 alkyl group, $R^3$ is a hydrogen atom or a C1–3 alkyl group, $R^4$ is a hydrogen atom or a C1–3 alkyl group, A is

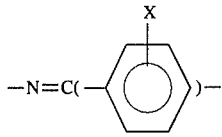

wherein X represents 1 to 5 carbon atoms or groups which may be the same or different and are selected from the group consisting of hydrogen atom, halogen atoms, C1–4 alkyl groups and C1–3 haloalkyl groups, and $R^5$ is a hydrogen atom), Y represents 1 to 5 carbon atoms or groups which may be the same or different and are selected from the group consisting of hydrogen atom, halogen atoms, cyano group and nitro group, Z represents 1 to 5 atoms or groups which may be the same or different and are selected from the group consisting of halogen atoms, C1–3 haloalkyl groups, C1–3 haloalkoxy groups, C1–3 alkylthio groups, C1–3 haloalkylthio groups, C1–3 alkylsulfinyl groups, C1–3 haloalkylsulfonyl groups, C1–3 haloalkylsulfinyl groups, and C1–3 alkylsulfonyl groups, and W is an oxygen atom.

3. A hydrazinecarboxamide derivative according to claim 2, wherein X is at the 3-position and Y or Z has a substituent at the 4-position.

4. An agricultural and horticultural insecticide composition comprising as an active ingredient a hydrazinecarboxamide derivative represented by the general formula (I):

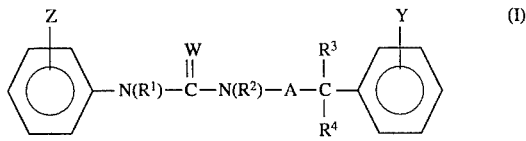

wherein $R^1$ is a hydrogen atom or a lower alkyl group, $R^2$ is a hydrogen atom or a lower alkyl group, $R^3$ is a hydrogen atom; a hydroxyl group; a lower alkyl group; a lower alkoxy group; a lower alkylcarbonyloxy group; an unsubstituted phenylcarbonyloxy group; or a substituted phenylcarbonyloxy group having on the phenyl ring 1 to 5 substituents which may be the same or different and are selected from the group consisting of halogen atoms, lower alkyl groups and lower haloalkyl groups, $R^4$ is a hydrogen atom or a lower alkyl group, $R^3$ and $R^4$ being able to be taken together to represent an oxygen atom, A is

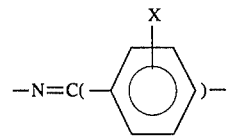

wherein X represents 1 to 5 atoms or groups which may be the same or different and are selected from the group consisting of hydrogen atom; hydroxyl group; halogen atoms; cyano group; lower alkyl groups; lower haloalkyl groups; lower alkoxy groups; lower haloalkoxy groups; lower alkoxyalkyl groups; lower alkenyloxy groups; cycloalkylcarbonyloxy groups; lower alkoxycarbonyloxy groups; lower alkoxycarbonylalkyloxy groups; lower alkylcarbonylalkyloxy groups; lower alkylsulfonyloxy groups; phenoxy group; methylenedioxy group; alkenylene groups having 3 to 4 carbon atoms so as to form a polycyclic ring together with the adjacent carbon atom of the phenyl ring; unsubstituted amino group; substituted amino groups having as the substituent(s) 1 or 2 lower alkyl groups which may be the same or different; substituted aminocarbonyloxy groups having as the substituent(s) 1 or 2 lower alkyl groups which may be the same or different; Y represents 1 to 5 atoms or groups which may be the same or different and are selected from the group consisting of hydrogen atom; hydroxyl group; halogen atoms; cyano group; nitro group; alkyl groups; lower haloalkyl groups; lower alkoxy groups; lower haloakoxy groups; lower alkenyloxy groups; lower alkylcarbonyloxy groups; lower alkylsulfonyloxy groups; lower haloalkylsulfonyloxy groups; lower alkylthio groups; lower haloalkylthio groups; lower alkylsulfinyl groups; lower haloalkylsulfinyl groups; lower alkylsulfonyl groups; lower haloalkylsulfonyl groups; lower alkoxycarbonyl groups; unsubstituted amino group; substituted amino groups having 1 or 2 substituents selected from the group consisting of formyl group, lower alkylcarbonyl groups, lower alkylsulfonyl groups, and substituted aminocarbonyl groups having as the substituent(s) one or more lower alkyl groups which may be the same or different; unsubstituted aminocarbonyl group; substituted aminocarbonyl groups having as the substituent(s) 1 or 2 lower alkyl groups which may be the same or different; or substituted aminosulfonyl groups having as the substituent(s) 1 or 2 lower alkyl groups which may be the same or different; phenyl group, Z represents 1 to 5 atoms or groups which may be the same or different and are selected from the group consisting of hydrogen atom; halogen atoms; cyano group; nitro group; alkyl groups; lower haloalkyl groups; unsubstituted cycloalkyl groups; substituted cycloalkyl groups having 1 to 5 substituents which may be the same or different and are selected from the group consisting of halogen atoms and lower alkyl groups; lower alkoxy groups; lower haloalkoxy groups; lower alkylthio groups; lower haloalkylthio groups; lower alkylsulfinyl groups; lower haloalkylsulfinyl groups; lower alkylsulfonyl groups; lower haloalkylsulfonyl groups; lower alkylcarbonyl groups; lower alkoxycarbonyl groups; lower alkylcarbonyloxy groups; lower alkylsulfonyloxy groups; lower haloalkylsulfonyloxy groups; unsubstituted phenoxy group; substituted phenoxy groups having 1 to 5 substituents which may be the same or different and are selected from the group consisting of halogen atoms, lower alkyl groups, lower haloalkyl groups, lower alkoxy groups and lower haloalkoxy groups; unsubstituted pyridyloxy group; substituted pyridyloxy groups having as the substituent(s) 1 to 4 atoms or groups which may be the same or different and are selected from the group consisting of halogen atoms, lower alkyl groups, lower haloalkyl groups, lower alkoxy groups and lower haloalkoxy groups, and W is an oxygen atom or a sulfur atom.

5. An agricultural and horticultural insecticide composition according to claim 4, wherein $R^1$ is a hydrogen atom or a lower alkyl group, $R^2$ is a hydrogen atom or a lower alkyl group, $R^3$ is a hydrogen atom or a lower alkyl group, $R^4$ is a hydrogen atom or a lower alkyl group, A is

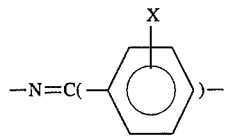

wherein X represents 1 to 5 atoms or groups which may be the same or different and are selected from the group consisting of hydrogen atom, halogen atoms, lower alkyl groups and lower haloalkyl groups, Y represents 1 to 5 atoms or groups which may be the same or different and are selected from the group consisting of hydrogen atom, halogen atoms, cyano group and nitro group, Z represents 1 to 5 atoms or groups which may be the same or different and are selected from the group consisting of hydrogen atom, halogen atoms, lower haloalkyl groups, lower haloalkoxy groups, lower alkylthio groups, lower haloalkylthio groups, lower alkylsulfonyl groups, lower haloalkylsulfinyl groups, lower alkylsulfonyl groups and lower haloalkylsulfonyl groups, and W is an oxygen atom.

6. An agricultural and horticultural insecticide composition according to claim 5, wherein X is at the 3-position and Y or Z has a substituent at the 4-position.

7. A process for controlling undesirable insect pests which comprises applying an agricultural and horticultural insecticide comprising as an active ingredient a hydrazinecarboxamide derivative represented by the general formula (I):

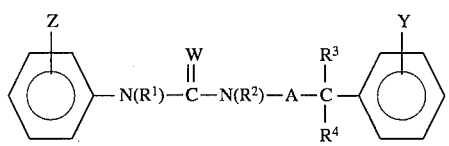

(I)

wherein $R^1$ is a hydrogen atom or a lower alkyl group, $R^2$ is a hydrogen atom or a lower alkyl group, $R^3$ is a hydrogen atom; a hydroxyl group; a lower alkyl group; a lower alkoxy group; a lower alkylcarbonyloxy group; an unsubstituted phenylcarbonyloxy group; or a substituted phenylcarbonyloxy group having on the phenyl ring 1 to 5 substituents which may be the same or different and are selected from the group consisting of halogen atoms, lower alkyl groups and lower haloalkyl groups, $R^4$ is a hydrogen atom or a lower alkyl group, $R^3$ and $R^4$ being able to be taken together to represent an oxygen atom, A is

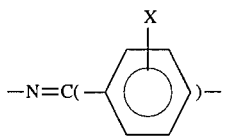

wherein X represents 1 to 5 atoms or groups which may be the same or different and are selected from the group consisting of hydrogen atom; hydroxyl group; halogen atoms; cyano group; lower alkyl groups; lower haloalkyl groups; lower alkoxy groups; lower haloalkoxy groups; lower alkoxyalkyl groups; lower alkenyloxy groups; cycloalkylcarbonyloxy groups; lower alkoxycarbonyloxy groups; lower alkoxycarbonylalkyloxy groups; lower alkylcarbonylalkyloxy groups; lower alkylsulfonyloxy groups; phenoxy group; methylenedioxy group; alkenylene groups having 3 to 4 carbon atoms so as to form a polycyclic ring together with the adjacent carbon atom of the phenyl ring; unsubstituted amino group; substituted amino groups having as the substituent(s) 1 or 2 lower alkyl groups which may be the same or different; substituted aminocarbonyloxy groups having as the substituent(s) 1 or 2 lower alkyl groups which may be the same or different; Y represents 1 to 5 atoms or groups which may be the same or different and are selected from the group consisting of hydrogen atom; hydroxyl group; halogen atoms; cyano group; nitro group; alkyl groups; lower haloalkyl groups; lower alkoxy groups; lower haloalkoxy groups; lower alkenyloxy groups; lower alkylcarbonyloxy groups; lower alkylsulfonyloxy groups; lower haloalkylsulfonyloxy groups; lower alkylthio groups; lower haloalkylthio groups; lower alkylsulfinyl groups; lower haloalkylsulfinyl groups; lower alkylsulfonyl groups; lower haloalkylsulfonyl groups; lower alkoxycarbonyl groups; unsubstituted amino group; substituted amino groups having 1 or 2 substituents selected from the group consisting of formyl group, lower alkylcarbonyl groups, lower alkylsulfonyl groups, and substituted aminocarbonyl groups having as the substituent(s) one or more lower alkyl groups which may be the same or different; unsubstituted aminocarbonyl group; substituted aminocarbonyl groups having as the substituent(s) 1 or 2 lower alkyl groups which may be the same or different; or substituted aminosulfonyl groups having as the substituent(s) 1 or 2 lower alkyl groups which may be the same or different; phenyl group, Z represents 1 to 5 atoms or groups which may be the same or different and are selected from the group consisting of hydrogen atom; halogen atoms; cyano group; nitro group; alkyl groups; lower haloalkyl groups; unsubstituted cycloalkyl groups; substituted cycloalkyl groups having 1 to 5 substituents which may be the same or different and are selected from the group consisting of halogen atoms and lower alkyl groups; lower alkoxy groups; lower haloalkoxy groups; lower alkylthio groups; lower haloalkylthio groups; lower alkylsulfinyl groups; lower haloalkylsulfinyl groups; lower alkylsulfonyl groups; lower haloalkylsulfonyl groups; lower alkylcarbonyl groups; lower alkoxycarbonyl groups; lower alkylcarbonyloxy groups; lower alkylsulfonyloxy groups; lower haloalkylsulfonyloxy groups; unsubstituted phenoxy group; substituted phenoxy groups having 1 to 5 substituents which may be the same or different and are selected from the group consisting of halogen atoms, lower alkyl groups, lower haloalkyl groups, lower alkoxy groups and lower haloalkoxy groups; unsubstituted pyridyloxy group; substituted pyridyloxy groups having as the substituent(s) 1 to 4 atoms or groups which may be the same or different and are selected from the group consisting of halogen atoms, lower alkyl groups, lower haloalkyl groups, lower alkoxy groups and lower haloalkoxy groups, and W is an oxygen atom or a sulfur atom) in an amount of 0.1 g to 5 kg in terms of the active ingredient per 10 ares in order to protect useful crops against undesirable insect pests.

* * * * *